United States Patent
Toste et al.

(10) Patent No.: US 11,332,482 B2
(45) Date of Patent: May 17, 2022

(54) AU(III) COMPLEXES FOR [18F] TRIFLUOROMETHYLATION AND METHODS FOR PRODUCING THE SAME

(71) Applicant: The Regents of the University of California, Oakland, CA (US)

(72) Inventors: F. Dean Toste, Piedmont, CA (US); Mark Daniel Levin, Chicago, IL (US); James Patrick O'Neil, San Leandro, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 156 days.

(21) Appl. No.: 16/615,248

(22) PCT Filed: May 21, 2018

(86) PCT No.: PCT/US2018/033677
§ 371 (c)(1),
(2) Date: Nov. 20, 2019

(87) PCT Pub. No.: WO2018/217637
PCT Pub. Date: Nov. 29, 2018

(65) Prior Publication Data
US 2020/0172557 A1      Jun. 4, 2020

Related U.S. Application Data

(60) Provisional application No. 62/509,230, filed on May 22, 2017.

(51) Int. Cl.
| | | |
|---|---|---|
| *A61K 51/00* | (2006.01) | |
| *A61M 36/14* | (2006.01) | |
| *C07F 1/00* | (2006.01) | |
| *A61K 51/04* | (2006.01) | |

(52) U.S. Cl.
CPC ............ *C07F 1/00* (2013.01); *A61K 51/0497* (2013.01)

(58) Field of Classification Search
CPC ............................. C07F 1/00; A61K 51/0497

USPC ......................................................... 424/1.89
See application file for complete search history.

(56) References Cited

U.S. PATENT DOCUMENTS

2014/0100377 A1    4/2014 Packard et al.

OTHER PUBLICATIONS

Harrison et al. Organometallics 2013, 32, 12-15. (Year: 2013).*
Akhmadullina et al. Russian J. Coord. Chem. 2012, 38, 589-595. (Year: 2012).*
Winston et al. J. Am. Chem. Soc. 2015, 137, 7921-7928. (Year: 2015).*
Lee et al. J. Organometallic Chem. 2017, 847, 270-277. (Year: 2017).*
Gil-Rubio, Juan & Vicente, Jose. (2015). Gold Trifluoromethyl Complexes. Dalton transactions (Cambridge, England : 2003). 44. 10.1039/c5dt02023a.
Lien, Vegard & Riss, P. (2014). Radiosynthesis of [ 18 F]Trifluoroalkyl Groups: Scope and Limitations. BioMed research international. 2014. 380124. 10.1155/2014/380124.
Blaya, María & Bautista, Delia & Gil-Rubio, Juan & Vicente, Jose. (2014). Synthesis of Au(I) Trifluoromethyl Complexes. Oxidation to Au(III) and Reductive Elimination of Halotrifluoromethanes. Organometallics. 33. 6358-6368. 10.1021/om500669j.
Huynh, Han & Guo, Shuai & Wu, Wenqin. (2013). Detailed Structural, Spectroscopic, and Electrochemical Trends of Halido Mono- and Bis(NHC) Complexes of Au(I) and Au(III). Organometallics. 32. 4591-4600. 10.1021/om400563e.
International Search Report and Written Opinion for PCT/US18/33677, dated Aug. 6, 2018, ISA/US, copy consists of 6 pages.

* cited by examiner

*Primary Examiner* — Michael G. Hartley
*Assistant Examiner* — Sean R Donohue

(57) ABSTRACT

Au(III) complexes for [$^{18}$F] trifluoromethylation and methods for producing the same are disclosed. A gold complex comprises $Au(CF_3)_2LR$, wherein L comprises a solubility supporting ligand and R comprises an organic substituent. The Au(III) complex can be used to prepare a positron emitting isotope that can be used as tracers for positron emitting tomography (PET) scans.

7 Claims, 22 Drawing Sheets

| Reg | Start (mm) | Stop (mm) | Centroid (mm) | $R_F$ | Region Counts | Region CPM | Pct of Total | Pct of ROI |
|---|---|---|---|---|---|---|---|---|
| Rgn 1 | 13.1 | 28.8 | 19.9 | -0.002 | 124953 | 124953 | 73.79 | 75.66 |
| Rgn 2 | 33.3 | 48 | 39.7 | 0.329 | 40200 | 40200 | 23.74 | 24.34 |
| 2 Peaks | | | | | 165153 | 165153 | 97.52 | 100 |

| Reg | Start (mm) | Stop (mm) | Centroid (mm) | $R_F$ | Region Counts | Region CPM | Pct of Total | Pct of ROI |
|---|---|---|---|---|---|---|---|---|
| Rgn 1 | 8.7 | 35.8 | 23 | 0.06 | 256667 | 256667 | 76.44 | 76.68 |
| Rgn 2 | 34.9 | 57.6 | 43.5 | 0.47 | 78048 | 78048 | 23.24 | 23.32 |
| 2 Peaks | | | | | 334715 | 334715 | 99.68 | 100 |

…

AU(III) COMPLEXES FOR [18F] TRIFLUOROMETHYLATION AND METHODS FOR PRODUCING THE SAME

CROSS REFERENCE TO RELATED APPLICATIONS

This application claims priority under 35 U.S.C. § 119(e) to U.S. provisional patent application Ser. No. 62/509,230, filed on May 22, 2017, which is hereby incorporated by reference in its entirety.

REFERENCE TO GOVERNMENT FUNDING

This invention was made with Government support under GM118190, awarded by the National Institutes of Health and under DE-AC02-05CH11231 awarded by the Department of Energy. The Government has certain rights in the invention.

FIELD OF THE INVENTION

The present disclosure relates generally to Au(III) complexes for [18F] Trifluoromethylation and methods for producing the same.

BACKGROUND

Certain compounds called "tracers" are used for positron emission tomography (PET) or PET scans. Generating the compounds that can be used as tracers in the PET scans can be challenging. For example, the compounds may be based off of certain chemical positron emitting isotopes with short half-lives, such as fluorine 18 ($^{18}$F) or carbon 11 ($^{11}$C), for example. For example, these positron emitting isotopes can have half-lives as short as 110 minutes.

As a result, there are challenges to current techniques to prepare the tracers used for PET scans. For example, the positron emitting isotopes need to be installed and given to the patient before the half-life of the isotope expires (e.g., within 110 minutes).

BRIEF DESCRIPTION OF THE DRAWINGS

The teaching of the present disclosure can be readily understood by considering the following detailed description in conjunction with the accompanying drawings, in which.

To facilitate understanding, identical reference numerals have been used, where possible, to designate identical elements that are common to the figures.

DETAILED DESCRIPTION

The present disclosure provides a new gold complex, precursor and processes for producing the same. The gold complex and precursors of the present disclosure can be activated to generate [18F] Trifluoromethyl compounds that can be used for various different applications, such as, tracers used in positron emission tomography (PET) scans.

The dual nature of the trifluoromethyl substituent as both crucial pharmaceutical functional group and synthetic frustration stems from a common cause: strong, non-interacting C—F bonds lend metabolic stability while simultaneously limiting the ability for chemical transformations to forge the relevant bonds and install the $CF_3$ unit. Generally speaking, nucleophilic (i.e. the Ruppert-Prakash reagent) or metal mediated (e.g. $CuCF_3$) chemistry is employed to deliver a preformed $CF_3$ unit to an organic substrate, though the latter class of chemistries is often plagued by the slow direct reductive elimination of fluoroalkyl ligands. Nonetheless, these modern protocols have aided the continuing proliferation of trifluoromethyl containing compounds in medicinal chemistry, including several high-profile blockbuster drugs.

Figure 1:
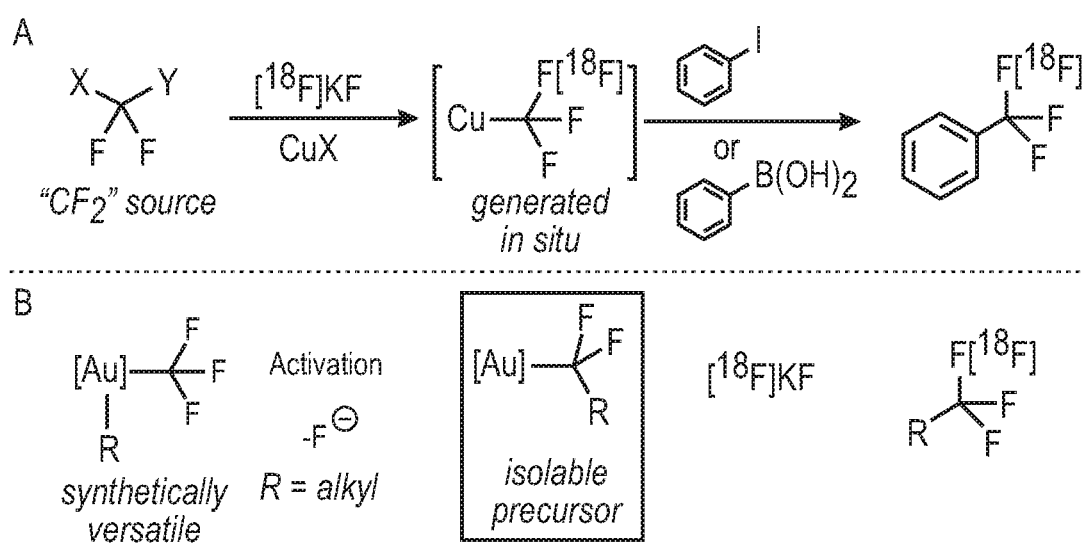
FIG. 1 illustrates an example retrosynthetic paradigm for CF$_3$ radiosynthesis using copper.

When these same synthetic considerations are extended towards synthesis of radiolabeled PET tracers containing $^{18}$F isotopes, the situation becomes more complex. As noted above, the biomedical applications of positron emission tomography (PET) rely upon the availability of radiolabeled tracers in which a radioactive positron emitting isotope, most commonly [$^{18}$F] (half-life ($t_{1/2}$)~110 min), is incorporated into a molecule of biological importance. These compounds can be used for high-resolution real-time imaging of tissue-level phenomena, enabling direct interrogation of disease states and mechanisms of bioactivity. However, nucleophilic substitution (i.e. $S_N2$ or $S_NAr$) chemistry, employed for the majority of organic fluoride radiosynthesis, is generally incompatible with the stereoelectronic demands of the $CF_3$ unit. Rather, in the most successful copper-mediated technology, a "$CF_2$" precursor is reacted with radiofluoride to generate the relevant $CF_3$ unit prior to incorporation into the tracer via organometallic intermediates. Reaction A of FIG. 1 illustrates an example of this reaction.

An isolable yet reactive difluoroalkyl metal substituent which affords the corresponding $CF_3$ unit upon treatment with radiofluoride would represent an alternative retrosynthetic paradigm by which to access these important tracer compounds. The present disclosure provides a class of Au(III) complexes which match exactly this profile of reactivity, simultaneously providing synthetic access to the requisite precursors and enabling their implementation for radiofluorination, as shown in reaction B of FIG. 1. The development of this advance has depended on detailed mechanistic investigation of an unexpected trifluorometh-ylated compound observed upon treatment of a complex 1a with $B(C_6F_5)_3$ (2) that is illustrated in reaction A of FIG. 2, namely the formal product of $C(sp^3)$-$CF_3$ reductive elimination from the gold center. It should be noted that some compounds are abbreviated with numbers as labeled in the figures or after the compound name illustrated and described in the examples below.

Figure 24:
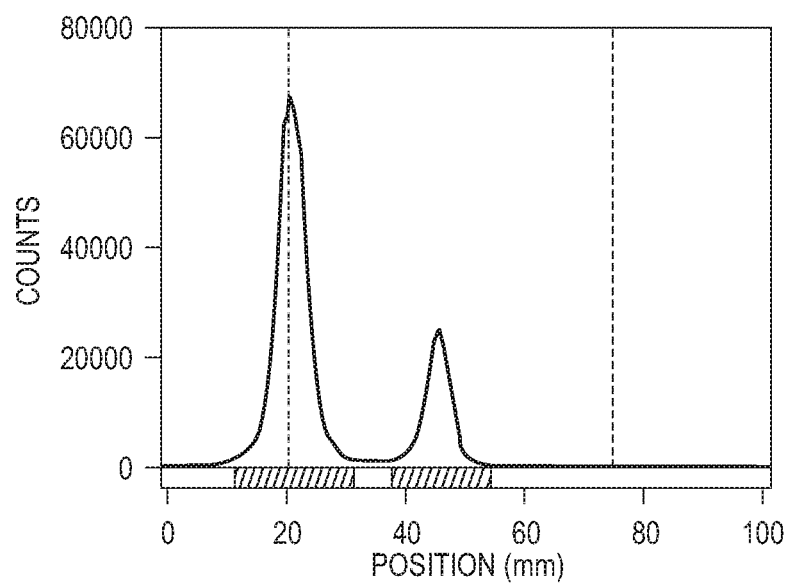
FIG. 24 illustrates a graphical representation of total counts of a first run for radiochemical conversion of [$^{18}$F]-5,5,5-trifluoropentyl 2-naphthoate.
Figure 25:
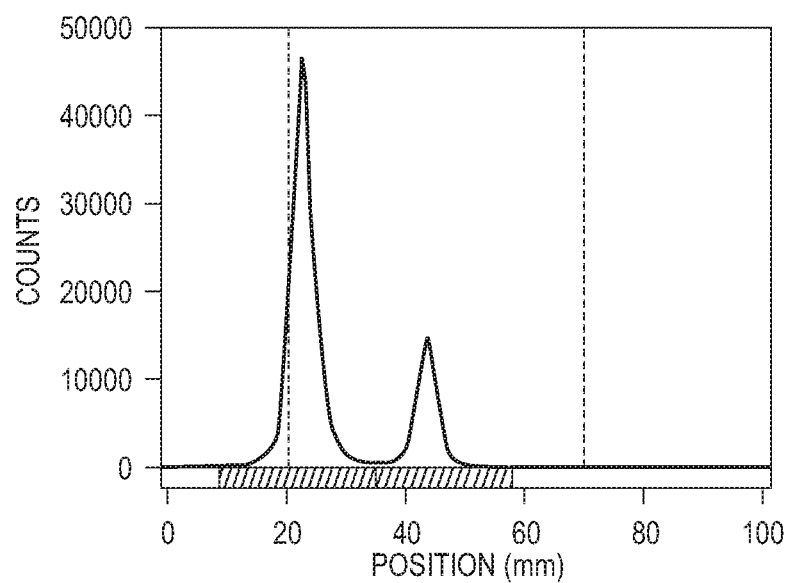
FIG. 25 illustrates a graphical representation of total counts of a second run for radiochemical conversion of [$^{18}$F]-5,5,5-trifluoropentyl 2-naphthoate.
Figure 26:
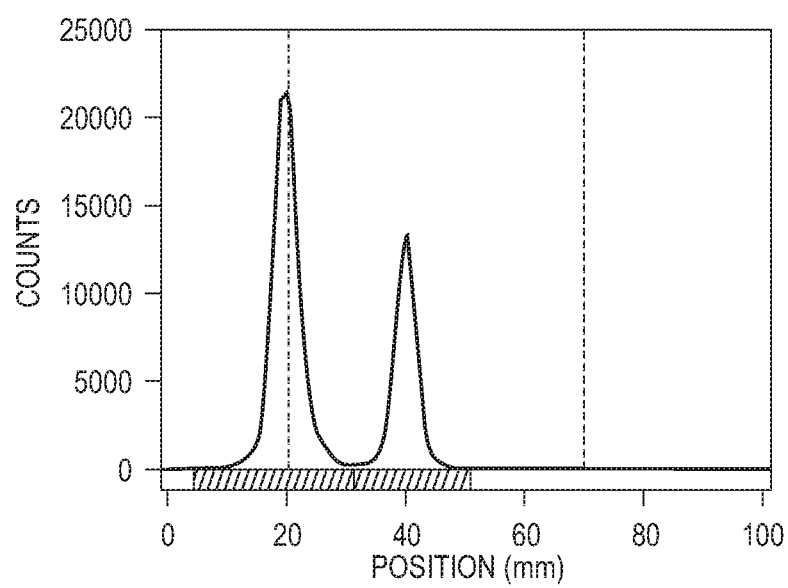
FIG. 26 illustrates a graphical representation of total counts of a third run for radiochemical conversion of [$^{18}$F]-5,5,5-trifluoropentyl 2-naphthoate.

In one example, $^{19}$F-NMR monitoring was performed on the formal reductive elimination of Me-$CF_3$ from the complex 1a in the presence of stoichiometric 2 at −15 degrees Celsius (° C.) to investigate the mechanism noted above. The reaction showed clean first-order kinetics (as shown in FIG. 26), consistent with catalytic action of 2. At catalytic loadings of 2, IPr—Au—$CF_3$ (3a) was the major Au-containing product, with complete conversion observed in less than 5 minutes at room temperature. The same reactivity was observed with the related phosphine complex 1b illustrated in reaction A of FIG. 2. Addition of 10 equivalents $Me_3SiBr$ to the 2-catalyzed reductive elimination formed an isolable Au(III) complex (4), bearing bromide and α,α-difluoroethyl substituents, as a mixture of two coordination isomers, as shown in reaction B of FIG. 2. Treatment of 4 with AgF leads to the gradual formation of $MeCF_3$ and 3, as shown in reaction C of FIG. 2. Taken together, these results implicate an overall mechanism, as shown in reaction D of FIG. 2, in which fluoride abstraction (i) from a $CF_3$ moiety of 1 by the borane 2 results in an intermediate difluorocarbenoid (or alternatively the carbenium resonance form, shown) which undergoes migratory insertion (ii) of the alkyl fragment followed by formal C—F reductive elimination (iii) to afford trifluoroethane. Additional experiments in support of this proposal include the formation of $MeCF_2OTf$ when stoichiometric TMS-OTf is used in place of 2, as shown in FIG. 26, and the observation of an intermediate aquo complex of the migratory insertion product during low temperature kinetics in wet $CD_2Cl_2$, as shown in FIGS. 24, 25, 27, and 28.

To various extents, these elementary steps have been observed previously at gold; in particular, earlier work on C—F reductive elimination suggests that an outer-sphere mechanism with considerable carbocationic character is operative. Although migratory insertion at Au(III) is comparatively rarer, Density Functional Theory (DFT) calculations suggest that α-insertion to the difluorocarbene occurs readily ($\Delta H^\ddagger$<4 kcal/mol). Such a low barrier likely explains why competitive hydrolysis of the difluorocarbene, common in metal halocarbene complexes, is not observed here even in wet solvent. Regardless, this mechanism is unusual because it represents a formal $C(sp^3)$-$CF_3$ reductive elimination, itself rarely if ever observed, by a catalytic process involving iterative disassembly and reassembly of the $CF_3$ moiety.

Figure 3:
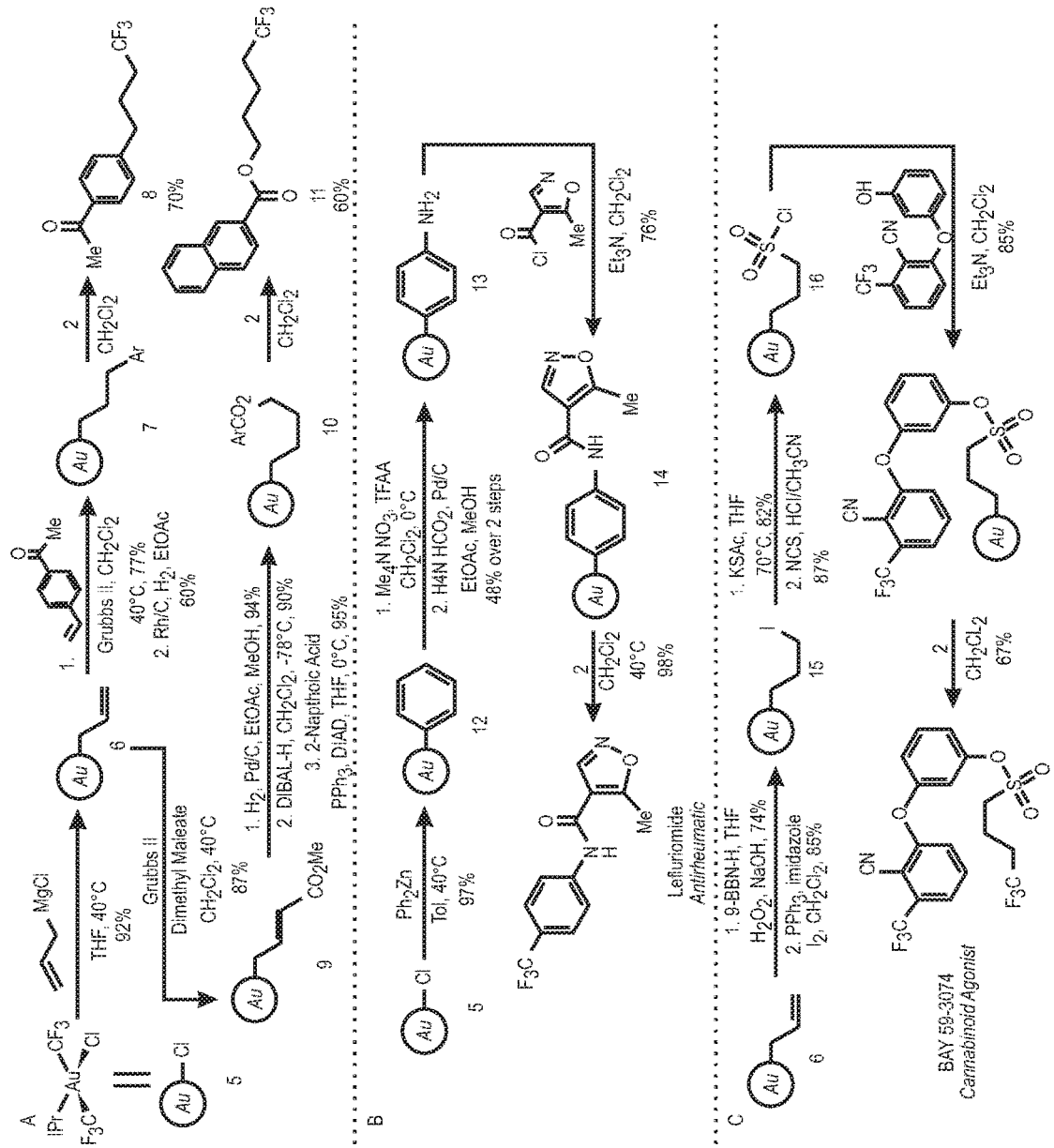
FIG. 3 illustrates examples of synthetic versatility of bis(trifluoromethyl) gold complexes.

It was noted that interception of the rebounding fluoride and introduction of a radiolabeled surrogate held promise for the synthesis of PET traces, provided that more complex organic substituents could be employed than the parent methyl in 1 of reaction A in FIG. 3. Diversification of the organic fragment beyond the simple methyl analogue was accomplished by means of a variety of synthetic manipulations (including hydroboration, cross-metathesis, hydrogenation, and aluminum hydride reduction) of η$^1$-allyl 6 of reaction A in FIG. 3, allowing the preparation of complex derivatives. Reductive elimination from the elaborated derivatives could likewise be triggered with 2 of reaction A of FIG. 3, ultimately affording reductive elimination products such as 8 and 11 of reaction A of FIG. 3. Similar diversity was seen in the chemistry of arylgold complex 12 of reaction B in FIG. 3 (including aromatic nitration without rupture of the gold-carbon bond), enabling the synthesis of Leflunomide via C—CF$_3$ reductive elimination from an advanced intermediate, as shown in FIG. 3B.

In order to further demonstrate the utility and functional group tolerance of this method, the Bayer lead compound BAY 59-3074 was prepared via straightforward elaboration of 6 of reaction C in FIG. 3. In addition to the depicted transformations, the complexes were also found to be tolerant of Simmons-Smith cyclopropanation, osmium-catalyzed dihydroxylation, periodate-mediated diol cleavage, and palladium-catalyzed cross coupling. Cleavage of the Au—C bond was only observed in the presence of exceptionally strong acids (CF$_3$SO$_3$H) and elemental halogens (e.g. Br$_2$). In addition, initial Au—C bond construction can also be achieved with dialkyl zinc or copper acetylide reagents, expanding the diversity of accessible structures (compounds S10 and S11, shown below). All of the intermediate gold complexes exhibited complete air and water tolerance, and were universally amenable to purification by silica gel column chromatography. As such, the Au moiety is regarded as a triggerable, but otherwise inert functional group, enabling routine chemical synthesis akin to typical organic substrates. Though synthetically tolerant metal complexes have been previously reported, such broad compatibility is rare, especially for Au(III), which tends to be highly sensitive toward reductive decomposition.

Figure 2:
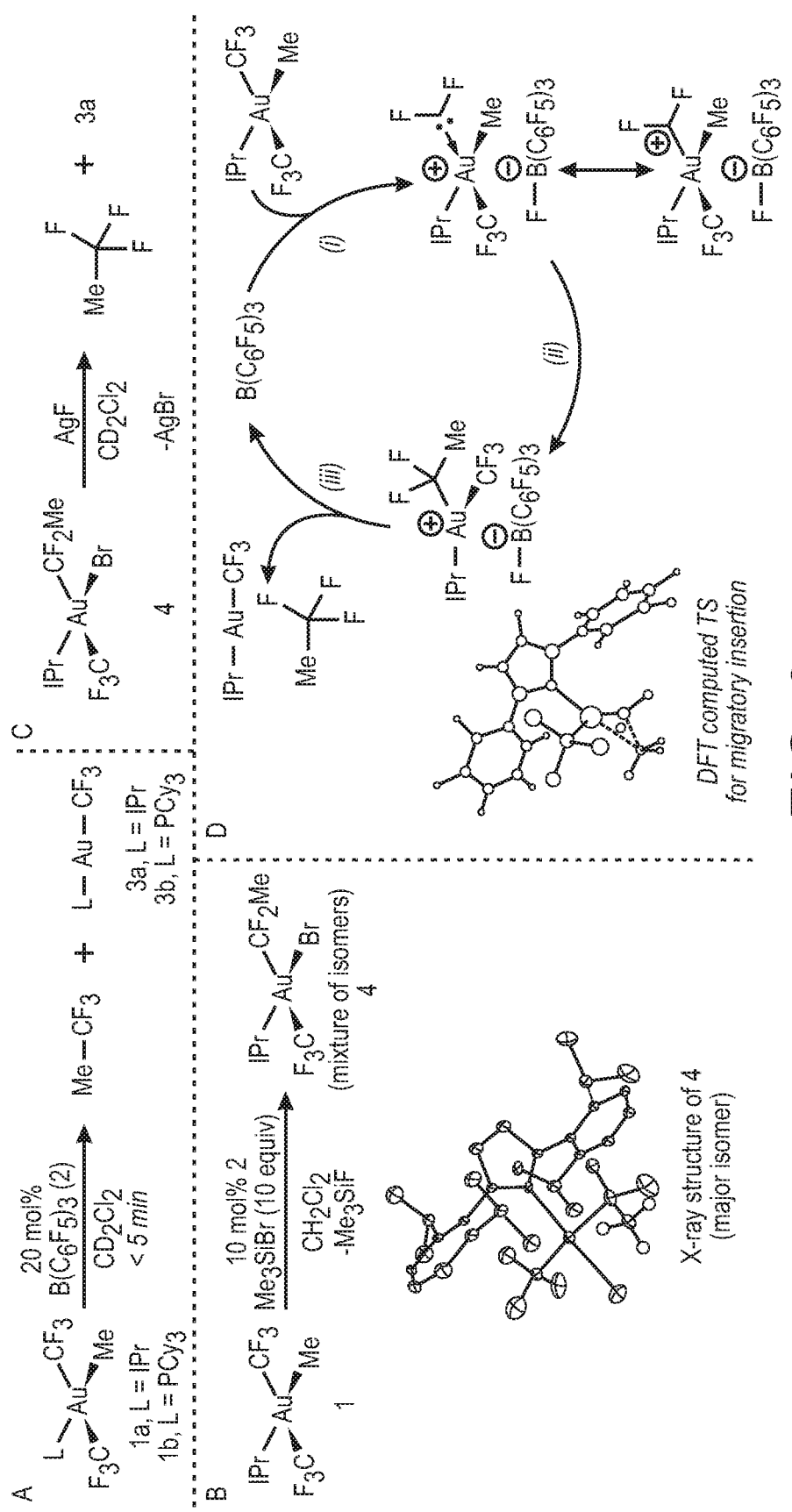
FIG. 2 illustrates an example discovery of formal C(sp$^3$)-CF$_3$ reductive elimination from Au(III) of the present disclosure.
Figure 4:
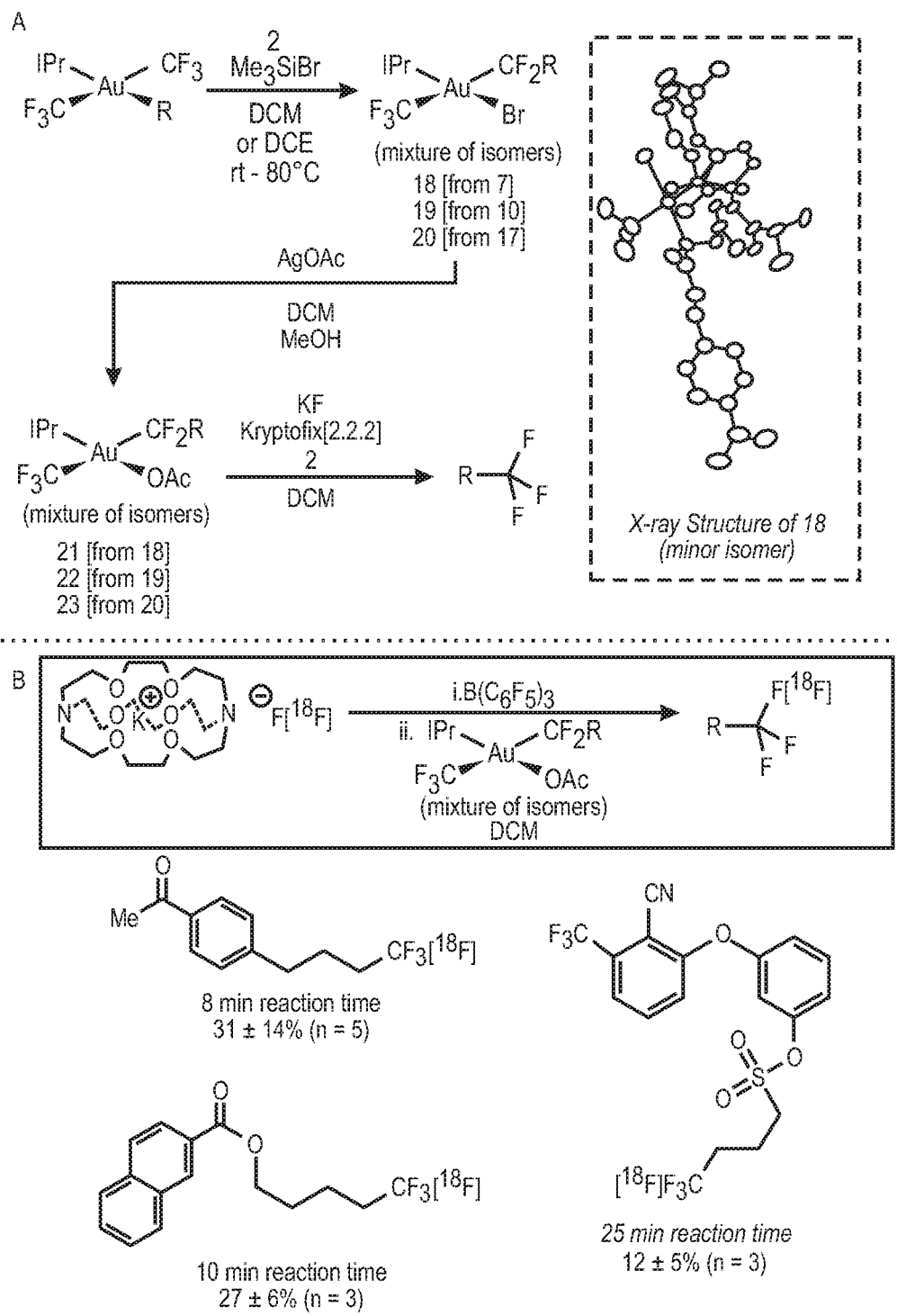
FIG. 4 illustrates an example of radiosynthesis via C-0F reductive elimination from Au(III) of the present disclosure.

For the radiochemical protocol, introduction of fluoride to complexes analogous to 4 in reactions A-C of FIG. 2 were initially envisioned. However, the silver mediated reductive elimination, as shown in reaction C of FIG. 2, was deemed too sluggish for these purposes, requiring the development of a modified strategy. Although complexes with several other counterions (such as triflate and tosylate) rapidly eliminated alkyl-CF$_2$X, the corresponding acetate complex exhibited an appropriate blend of stability and reactivity to enable nucleophilic reductive elimination when treated with 2, shown in reactions A and B of FIG. 2, and a suitable fluoride source. An example of the activation of the gold complex and the ligand exchange described above, is illustrated in reaction A of FIG. 4. Borane 2, shown in reaction A of FIG. 4, was required for rapid reductive elimination to occur; in its absence, the intermediate [Au(III)]-F persisted for long enough to be observed by $^{19}$F-NMR spectroscopy, and side-reactions arising from base-mediated decomposition or glass-etching occurred alongside slow reductive elimination, consistent with an outer-sphere mechanism for C—F bond formation assisted by 2. The combined protocol was directly translated to a radiological analogue, affording the corresponding radiolabeled reductive elimination products starting from KF and Kryptofix[2.2.2], as shown in reaction B of FIG. 4.

Several features of this protocol merit additional comment. First, aromatic complexes remain inaccessible for radiochemical functionalization by this method due to the rapid reductive elimination of the benzylic difluoroalkyl moiety; treatment of phenyl complex 10 with Me$_3$SiBr and 2 results in PhCF$_2$Br rather than an isolable Au(III) complex. As such, the scope of this protocol remains fully complementary to the corresponding Cu-mediated analogue via CuCF$_3$. Second, isolation of [$^{18}$F]-BAY 59-3074 by preparative HPLC afforded an isolated radiochemical yield of 6% and a specific activity of 8 millicurie per micro mol (mCi/μmol) starting from 71 mCi of [$^{18}$F]-fluoride. Such a specific activity is on par with that of many CuCF$_3$-based protocols, though values ranging from 2.7 to 860 mCi/μmol have been obtained depending on the preparative method; it should be noted that these are all much lower than classical nucleophilic substitution methodologies for alkyl fluoride synthesis (typically in excess of 1000 mCi/μmol), highlighting an important direction for future development of radiotrifluoromethylation. Finally, the cost associated with the use of stoichiometric organogold reagents, though substantial by the metrics of process-scale pharmaceutical preparation, are relatively small in this context given the low concentrations required, the cost of $^{18}$F production, and the costs of the associated medical imaging technology.

In any case, the protocol established here represents an important proof-of-concept, in the radiosynthesis of organic trifluoromethyl groups by a retrosynthetic paradigm involving C—F reductive elimination. The broader mechanistic framework consisting of fluoride-rebound reductive elimination upon which this radiochemical reaction is built should also have implications for the understanding of transition metal catalysis, as it seems probable that such a mechanism is in fact operative in the related copper-mediated protocols currently in use (both in the radiochemical and non-radiochemical contexts). Furthermore, the present disclosure suggests a promising direction for the development of organometallic reagents writ large via catalytically-triggered reductive elimination of functionally tolerant complexes.

EXAMPLES

Materials and Methods

Unless stated otherwise, all reactions were performed in oven-dried or flame-dried glassware. All glassware was cleaned using aqua regia to remove metal impurities. NMR Tubes used for reductive elimination studies with B(C$_6$F$_5$)$_3$ were additionally silylated with hexamethdisilazane at 100° C. prior to use. Reactions were sealed with rubber septa under a nitrogen atmosphere and were stirred with Teflon-coated magnetic stir bars. Dry tetrahydrofuran (THF), toluene (Tol), dimethylfomamide (DMF), acetonitrile (MeCN), triethylamine (TEA), diethyl ether (Et$_2$O), benzene (PhH), and dichloromethane (DCM) were obtained by passing these previously degassed solvents through activated alumina columns.

All other reagents were used as received, with the following exceptions: Tris(pentafluorophenyl) borane was purchased from Strem Chemical and purified by hot filtration and recrystallization from hexanes followed by vacuum sublimation at 100° C. Trimethylbromosilane was purified by distillation. Iodomethane was purified by passing neat over a pad of basic alumina. For all reactions conducted in a glovebox, reagents were thoroughly dried and degassed by standard methods prior to use.

Reactions were monitored by thin layer chromatography (TLC) on Silicycle Siliaplate™ glass backed TLC plates (250 μm thickness, 60 Å porosity, F-254 indicator) and visualized by UV irradiation or by staining as indicated. Volatile solvents were removed under reduced pressure with a rotary evaporator and dried on high vacuum on a Schlenk line. H NMR, C NMR, F NMR, and P NMR spectra were taken with Bruker spectrometers operating at 300, 400, 500, or 600 MHz for H. Chemical shifts are reported relative to the residual solvent signal (H NMR: δ=5.32; C NMR: δ=53.84 for DCM-d$_2$). NMR data are reported as follows:

chemical shift (multiplicity, coupling constants where applicable, number of hydrogens). Splitting is reported with the following symbols: s=singlet, bs=broad singlet, d=doublet, t=triplet, q=quartet, hept=heptet, m=multiplet. High-resolution mass spectra (HRMS) were performed on a Thermo LTQ-FT-ICR (7T, ESI) by the QB3 mass spectral facility at the University of California, Berkeley. Elemental Analyses were performed by the Microanalytical Facility at the University of California, Berkeley.

Chloro(dimethylsulfide)gold(I) was prepared by reduction of $AuCl_3$ (purchased from Strem) according previously reported procedures. Tetraphenylphosphonium bis(trifluoromethyl)aurate was prepared from chloro(dimethylsulfide)gold(I) and $TMSCF_3$ as previously reported and purified by repeated precipitation from DCM with diethyl ether.

Most of the gold complexes reported herein are moderately light sensitive, so reactions, work up procedures, and purifications were conducted with exclusion of light, and all complexes were stored wrapped in aluminum foil.

Synthetic Procedures

Tetraphenylphosphonium
Trans-Bis(Trifluoromethyl)Dichloroaurate, S1

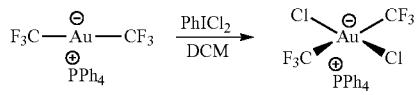

This compound was prepared using a modification of existing literature precedent. Treatment of a solution of tetraphenylphosphonium bis(trifluoromethyl)aurate (5.29 grams (g), 7.84 millimoles (mmol)) in dichloromethane (78 milliliter (mL), 0.1 molar (M)) with freshly prepared iodobenzene dichloride (4.31 g, 15.68 mmol, 2 equiv, added as a solid) resulted in immediate color change from colorless to yellow. The mixture was stirred for 30 minutes and concentrated. The crude solid was washed with copious diethyl ether, extracted with THF, and filtered. Concentration of the THF extract afforded the desired product as a colorless solid (5.8 g, 99% yield). Spectra were consistent with those previously reported.

Tetraphenylphosphonium
Trans-Bis(Trifluoromethyl)Methyliodoaurate, S2

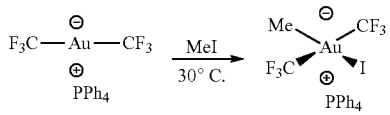

Tetraphenylphosphonium bis(trifluoromethyl)aurate (1.10 g, 1.6 mmol) was dissolved in iodomethane (30.1 mL, 410 mmol, 250 equiv), and the mixture was heated with stirring at 30° C. for 18 hours (hrs). The mixture was concentrated, extracted with dichloromethane, and filtered through a glass fiber filter. The filtrate was layered with diethyl ether, and placed in a freezer at −20° C., resulting in the formation of colorless crystals which were collected by filtration (1.18 g, 89% yield). X-ray quality crystals were grown by vapor diffusion of diethyl ether into a dilute dichloromethane solution.

trans-methylbis(trifluoromethyl)-1,3-Bis(2,6-diisopropylphenyl)-1,3-dihydro-2H-imidazol-2-ylidene-gold(III), 1a

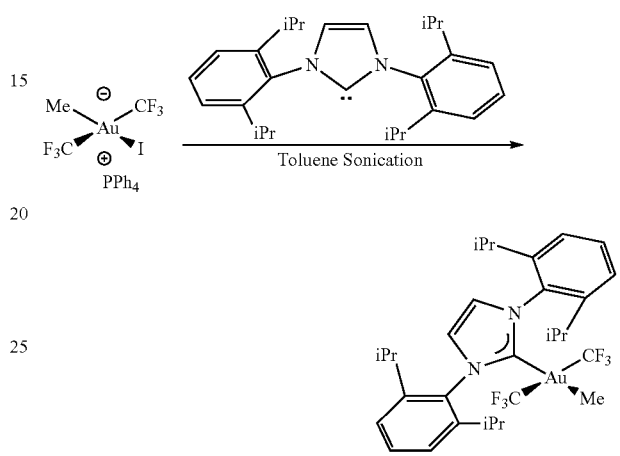

Figure 5:
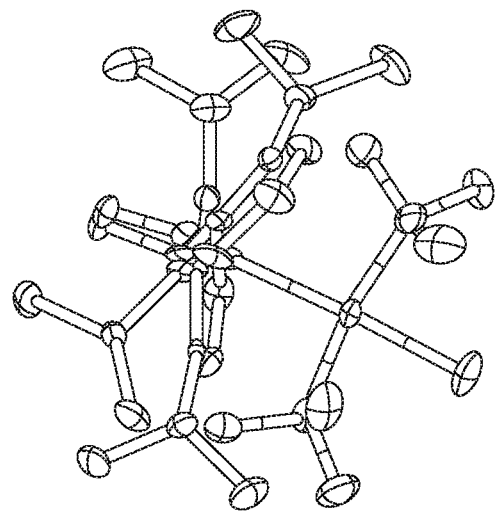
FIG. 5 illustrates an example three dimensional molecule model of trans-methylbis(trifluoromethyl)-1,3-Bis(2,6-diisopropylphenyl)-1,3-dihydro-2H-imidazol-2-ylidene-gold (III)

In a nitrogen-filled glovebox, S2 (245 milligrams (mg), 0.30 mmol, 1.05 equiv) was slurried in Toluene (5 mL) and a solution of IPr free carbene (113 mg, 0.29 mmol, 1.0 equiv) in Toluene (15 mL) was added. The mixture was sealed and brought out of the glovebox, sonicated for 8 minutes, and then stirred for an additional 20 minutes. The mixture was concentrated onto Silica, and purified by chromatography eluting with 5% diethyl ether in hexanes, affording the desired product as a colorless solid (179 mg, 81% yield). X-ray quality crystals were obtained by layering hexanes onto a solution of 1a in diethyl ether. A three dimensional molecule model is illustrated in FIG. 5.

Trans-Methylbis(Trifluoromethyl)-Tricyclohexylphosphine-Gold(III), 1b

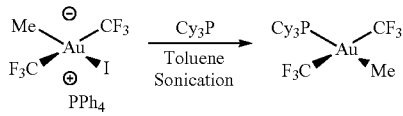

Figure 6:
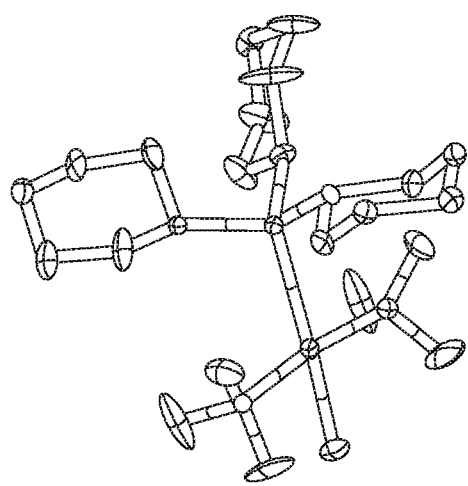
FIG. 6 illustrates an example three dimensional molecule model of trans-methylbis(trifluoromethyl)-tricyclohexylphosphine-gold(III)

In a nitrogen-filled glovebox, S2 (73 mg, 0.09 mmol, 1.05 equiv) was slurried in Toluene (5 mL) and a solution of tricyclohexylphosphine (24 mg, 0.085 mmol, 1.0 equiv) in Toluene (10 mL) was added. The mixture was sealed and brought out of the glovebox, sonicated for 8 minutes, and then stirred for an additional 20 minutes. The mixture was concentrated onto Silica, and purified by chromatography eluting with 5% diethyl ether in hexanes, affording the desired product as a colorless solid (52 mg, 99% yield). X-ray quality crystals were obtained by vapor diffusion of hexanes into a solution of 1b in THF. A three dimensional molecule model is illustrated in FIG. 6.

Bromo-(1,1-difluoroethyl)trifluoromethyl-1,3-Bis(2,6-diisopropylphenyl)-1,3-dihydro-2H-imidazol-2-ylidene-gold(III), 4

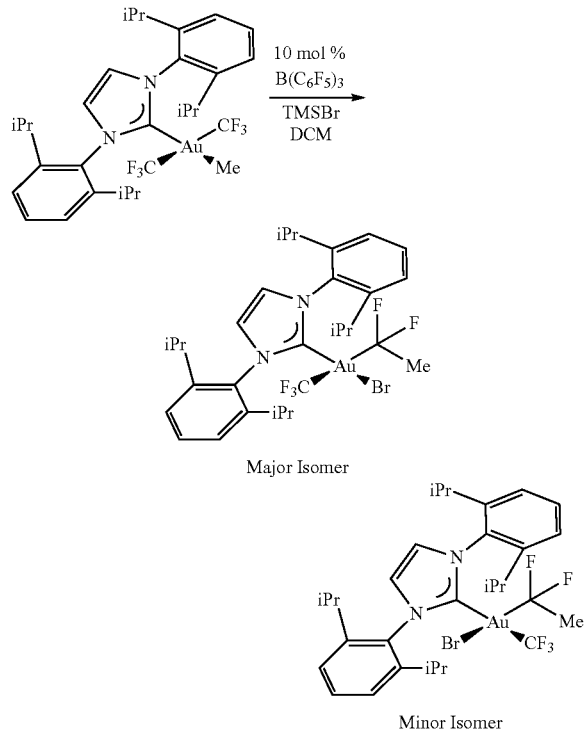

To a solution of 1a (370 mg, 0.5 mmol) in dichloromethane (20 mL) was added bromotrimethylsilane (0.66 mL, 5 mmol, 10 equiv) followed by a solution of tris(pentafluorophenyl)borane (25.6 mg, 0.05 mmol, 0.1 equiv, prepared in a nitrogen filled glovebox) in 5 mL of DCM. The mixture was monitored by TLC for consumption of starting material [Note: the rate varies depending on the purity of the silane and borane reagents].

Figure 7:
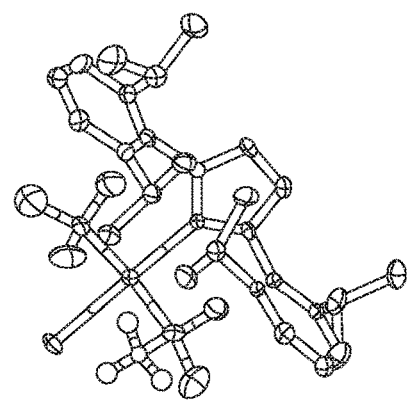
FIG. 7 illustrates an example three dimensional molecule model of Bromo-(1,1-difluoroethyl)trifluoromethyl-1,3-Bis(2,6-diisopropylphenyl)-1,3-dihydro-2H-imidazol-2-ylidene-gold(III)

After 45 minutes of stirring at room temperature, the mixture was quenched by the addition of saturated aqueous sodium bicarbonate. The layers were separated and the aqueous layer was extracted twice with additional dichloromethane. The combined organic fractions were dried over Na$_2$SO$_4$, filtered, and concentrated. The resulting mixture of isomers was purified by chromatography on silica gel eluting with a mixture of Hexanes/DCM/Et$_2$O (85/7.5/7.5) to afford the title compound as a colorless solid containing a mixture of isomers in a ~2:1 ratio (282 mg, 70%). A three dimensional molecule model is illustrated in FIG. 7.

For the purposes of characterization, the isomers can be carefully separated by repeated chromatography eluting with (90:5:5 Hexanes/DCM/Et$_2$O) to afford fractions of each isomer. Over the course of repeated chromatography additional decomposition byproducts are formed which have not been identified but which can be partially removed by subsequent recrystallization from PhH/Hexanes. The major isomer was assigned structurally by X-ray diffraction and by the CNMR shift for the carbene carbon which was consistent with a trans halide substituent (cf. 5 below). The minor isomer was assigned by its CNMR, which showed a quartet of triplets for the carbene carbon with ca. twice the coupling constant for C—CF$_3$ as for C—CF$_2$Me, as well as its 1D-NOE spectrum which showed an interaction between the isopropyl methine and the CF$_2$Me protons.

trans-chlorobis(trifluoromethyl)-1,3-Bis(2,6-diisopropylphenyl)-1,3-dihydro-2H-imidazol-2-ylidene-gold(III), 5

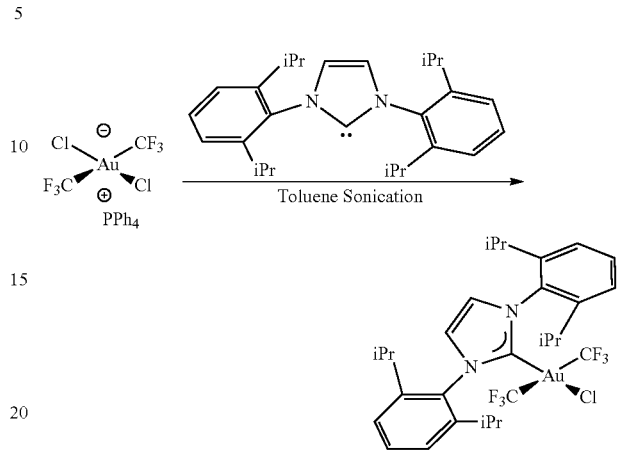

Figure 8:
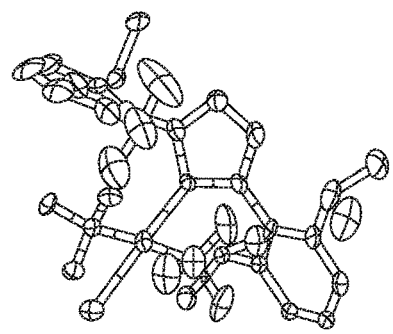
FIG. 8 illustrates an example three dimensional molecule model of trans-chlorobis(trifluoromethyl)-1,3-Bis(2,6-diisopropylphenyl)-1,3-dihydro-2H-imidazol-2-ylidene-gold (III)

In a nitrogen-filled glovebox, S1 (3.8 g, 5.04 mmol, 1 equiv) was slurried in Toluene (30 mL) and a solution of IPr free carbene (1.96 g, 5.04 mmol, 1 equiv) in Toluene (70 mL) was added. The mixture was sealed and brought out of the glovebox, sonicated for 8 minutes, and then stirred for an additional 1 hour. The mixture was concentrated onto Silica, and purified by chromatography eluting with 50% dichloromethane in hexanes, affording a pale yellow solid which was washed with hexanes to remove the co-eluting color impurity. This afforded the desired product as a colorless solid (3.2 g, 84% yield). X-ray quality crystals were obtained by vapor diffusion of hexanes into a saturated THF solution. A three dimensional molecule model is illustrated in FIG. 8.

trans-allylbis(trifluoromethyl)-1,3-Bis(2,6-diisopropylphenyl)-1,3-dihydro-2H-imidazol-2-ylidene-gold (III), 6

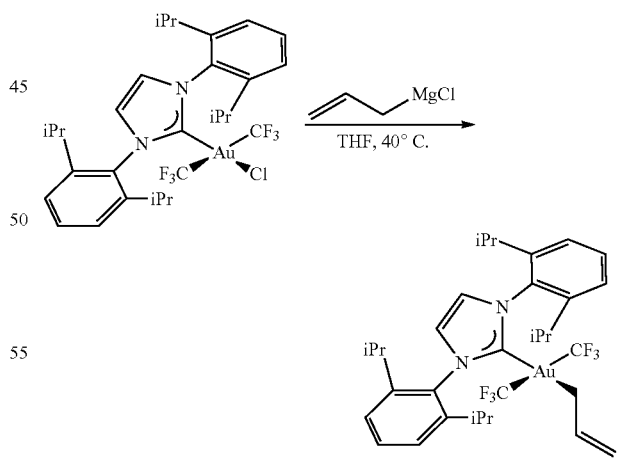

Figure 9:
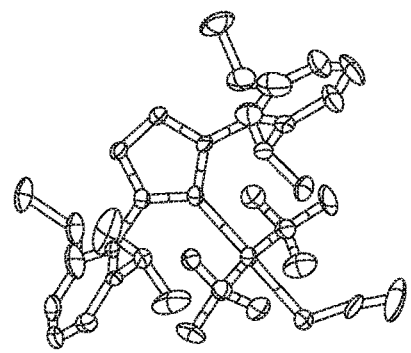
FIG. 9 illustrates an example three dimensional molecule model of trans-allylbis(trifluoromethyl)-1,3-Bis(2,6-diisopropylphenyl)-1,3-dihydro-2H-imidazol-2-ylidene-gold (III)

To a solution of 5 (1.0 g, 1.32 mmol) in THF (65 mL, 0.02 M) in a schlenk bomb was added allyl magnesium chloride (6.6 mL of a 2M THF solution, 13.2 mmol, 10 equiv). The flask was sealed with a teflon valve and heated at 40° C. for 12 hours. Upon cooling, the mixture was quenched with H$_2$O and extracted three times with diethyl ether. The combined organic extracts were dried with sodium sulfate, filtered, and concentrated. The crude material was purified by silica gel chromatography eluting with 70:30 Hexanes/ DCM yielding the title compound as a colorless solid (930 mg, 92%). A three dimensional molecule model is illustrated in FIG. 9.

trans-(E)-(3-(4-acetylphenyl)allyl)-bis(trifluoromethyl)-1,3-Bis(2,6-diisopropylphenyl)-1,3-dihydro-2H-imidazol-2-ylidene-gold(III), S3

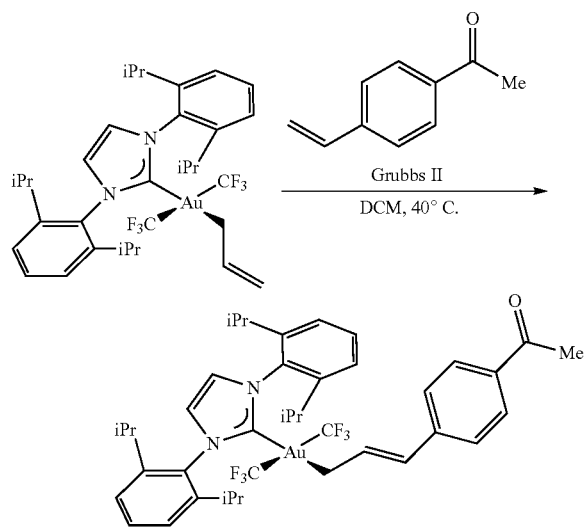

6 (529 mg, 0.693 mmol), 4-vinylacetophenone (405 mg, 2.77 mmol, 4 equiv), and Grubbs 2$^{nd}$ Generation Catalyst (25 mg, 0.035 mmol, 5 mol %) were weighed into a Schlenk bomb. Dichloromethane (18 mL) was added, the flask was sealed and the mixture was heated at 40° C. for 12 hours. The mixture was concentrated onto silica gel and purified by chromatography eluting on a gradient from 90:5:5 Hex/DCM/Et$_2$O to 80:10:10 Hex/DCM/Et$_2$O affording 468 mg of the title compound as a colorless solid alongside 88 mg of starting material (76% yield, 91% brsm). Recrystallization from Et$_2$O/Hexanes at −20° C. affords the diethyl ether solvate.

trans-(3-(4-acetylphenyl)propyl)-bis(trifluoromethyl)-1,3-Bis(2,6-diisopropylphenyl)-1,3-dihydro-2H-imidazol-2-ylidene-gold(III), 7

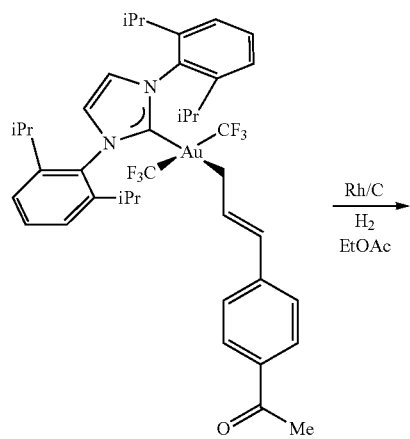

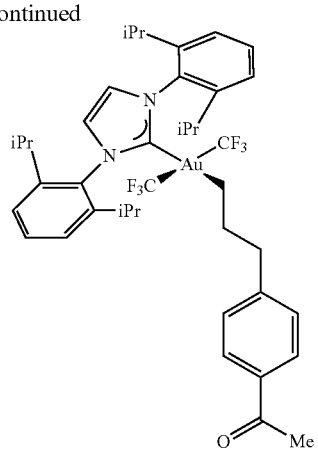

Figure 10:
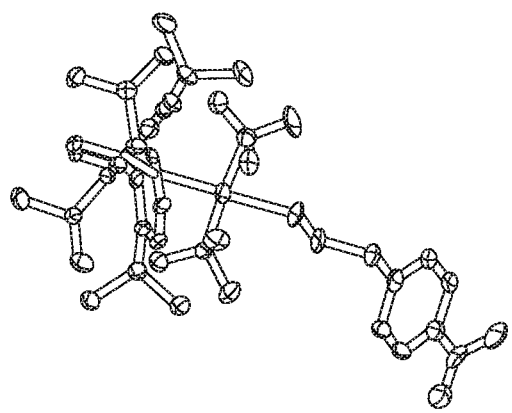
FIG. 10 illustrates an example three dimensional molecule model of trans-(3-(4-acetylphenyl)propyl)-bis(trifluoromethyl)-1,3-Bis(2,6-diisopropylphenyl)-1,3-dihydro-2H-imidazol-2-ylidene-gold(III)

S3 (468 mg, 0.53 mmol) was dissolved in ethyl acetate (50 mL, 0.01 M) and rhodium on carbon (109 mg of 5 wt %, 10 mol % Rh) was added. The mixture was sparged with N$_2$ with stirring for 10 minutes, then with H$_2$ (via balloon) for 10 minutes. The mixture was left under a static atmosphere of H$_2$ and monitored by TLC, staining with p-Anisaldehyde (the two compounds are co-polar, but the starting complex stains pink and the product stains orange upon heating). After 6.5 hours, consumption of starting material was observed, and H$_2$ was removed by sparging with N$_2$. The mixture was filtered through a pad of celite eluting with ethyl acetate and concentrated onto silica gel. Chromatography eluting with 85:7.5:7.5 Hexanes/DCM/Et$_2$O afforded the title compound as a colorless solid (274 mg, 60% yield). A three dimensional molecule model is illustrated in FIG. 10.

Alternate Procedure:

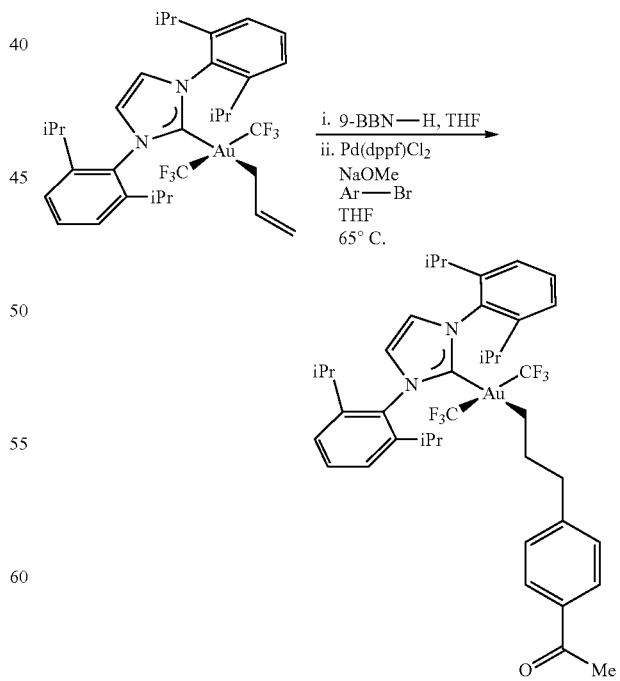

In a nitrogen filled glovebox, to 6 (0.11 mmol, 84 mg) was added 9-BBN—H (0.95 equiv, 12.7 mg) and THF (3 mL).

The mixture was stirred overnight, and then Pd(dppf)Cl$_2$ (2.5 mg, 3 mol %), NaOMe (18 mg, 3 equiv), and 4-acetylbromobenzene (25 mg, 1.1 equiv) were added. The mixture was heated at 65° C. for 1.5 hours and then concentrated. The crude product was purified by column chromatography eluting with 85:7.5:7.5 Hexanes/DCM/Et$_2$O afforded the title compound as a colorless solid (42 mg, 44% yield). It should be noted that though more rapid than the 2 step metathesis/hydrogenation procedure, this procedure was found to be less reliable for large scale synthesis of the desired compound.

Bromo-((4-(4-acetylphenyl)-1,1-difluorobutyl))-trifluoromethyl-1,3-Bis(2,6-diisopropylphenyl)-1,3-dihydro-2H-imidazol-2-ylidene-gold(III) (Mixture of Coordination Isomers), 18

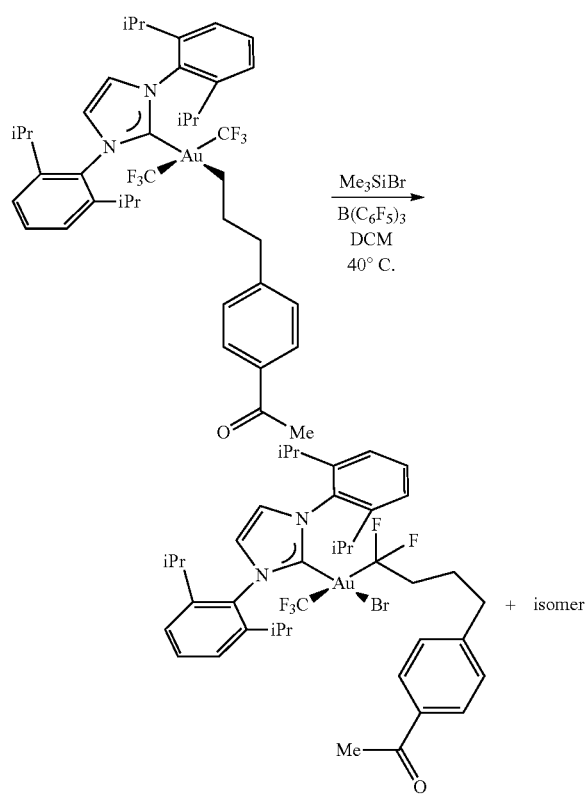

To a solution of 7 (160 mg, 0.18 mmol) in dichloromethane (5 mL) in a schlenk bomb was added bromotrimethylsilane (0.24 mL, 1.81 mmol, 10 equiv) followed by tris(pentafluorophenyl) borane (46 mg, 0.09 mmol, 50 mol %) in dichloromethane (4 mL). The mixture was sealed with a teflon valve and heated at 40° C. for 24 hours. Saturated aqueous sodium bicarbonate was added, and the layers were separated. The aqueous layer was extracted 3× with DCM, and the combined organic layers were dried over Na$_2$SO$_4$, filtered, and concentrated. The crude residue was purified by column chromatography on SiO$_2$, eluting on a gradient from 85:7.5:7.5 to 80:10:10 Hexanes/DCM/Et$_2$O affording 105 mg of the title compound as a 55:45 mixture of two isomers as well as 36 mg of recovered starting material (61% yield, 78% brsm).

Figure 11:
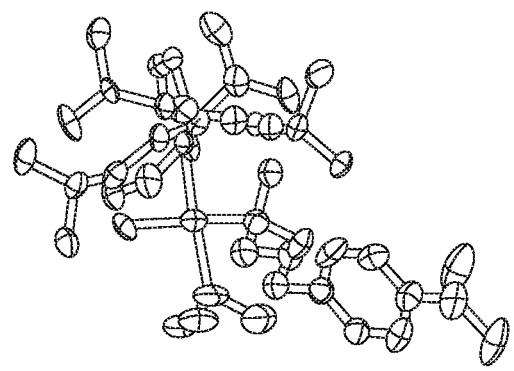
FIG. 11 illustrates an example three dimensional molecule model of trans Bromo-((4-(4-acetylphenyl)-1,1-difluorobutyl))-trifluoromethyl-1,3-Bis(2,6-diisopropylphenyl)-1,3-dihydro-2H-imidazol-2-ylidene-gold(III)
Figure 12:
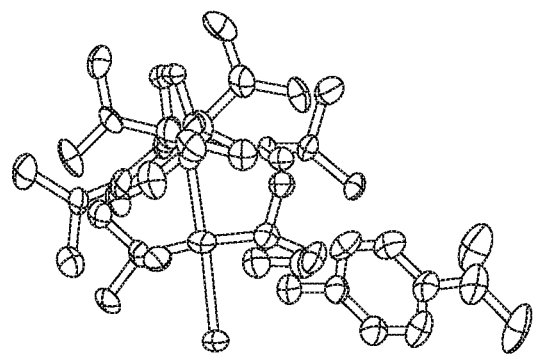
FIG. 12 illustrates an example three dimensional molecule model of cis Bromo-((4-(4-acetylphenyl)-1,1-difluorobutyl))-trifluoromethyl-1,3-Bis(2,6-diisopropylphenyl)-1,3-dihydro-2H-imidazol-2-ylidene-gold(III)

The trans isomer crystallizes preferentially from Toluene/Hexanes, but does not afford material of sufficient isomeric purity for characterization purposes. A three dimensional molecule model is illustrated in FIG. 11. A hexanes extract of a mixture enriched in the cis isomer gave a co-crystal of isomers suitable for X-ray diffraction upon slow evaporation. A three dimensional molecule model is illustrated in FIG. 12. These data were modeled to extract structures for each isomer by accounting for substitutional disorder and refined to an occupancy of approximately 60/40 favoring the trans isomer.

Acetato-((4-(4-acetyl phenyl)-1,1-difluorobutyl))-trifluoromethyl-1,3-Bis(2,6-diisopropylphenyl)-1,3-dihydro-2H-imidazol-2-ylidene-gold(III) (Mixture of Coordination Isomers), 21

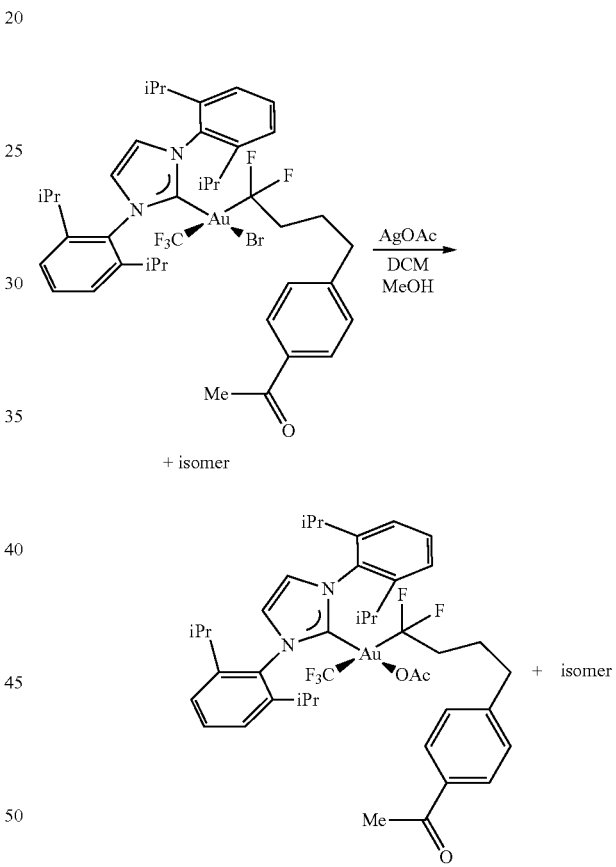

18 (130 mg, 0.137 mmol) was dissolved in dichloromethane (1.8 mL) and methanol (18 mL) and silver acetate (227 mg, 1.37 mmol, 10 equiv) was added. The mixture was sonicated briefly and stirred for 12 hours at room temperature in the dark. The mixture was filtered, and the filter cake was washed with dichloromethane. The combined filtrates were concentrated, and the residue was again extracted with dichloromethane, filtered and concentrated affording the product as a colorless solid (126 mg). The resulting product was used as soon as possible without further purification. Storage, even at −20° C. results in the gradual reductive elimination of R—CF$_2$OAc.

trans-(E)-(4-methoxy-4-oxobut-2-en-1-yl)-bis(trifluoromethyl)-1,3-Bis(2,6-diisopropylphenyl)-1,3-dihydro-2H-imidazol-2-ylidene-gold(III), 9

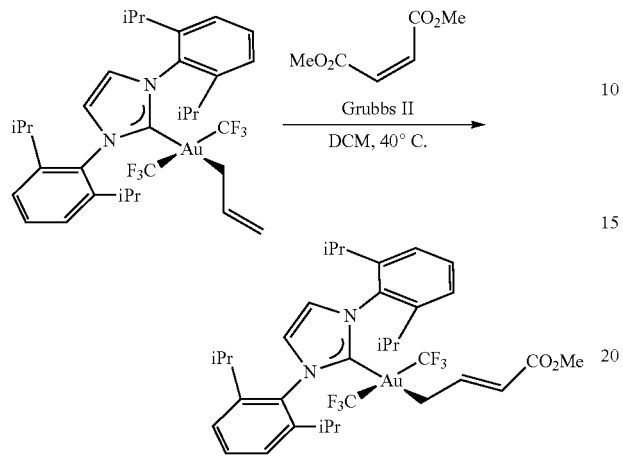

6 (76 mg, 0.1 mmol), and Grubbs $2^{nd}$ Generation Catalyst (3 mg, 3 mol %) were weighed into a Schlenk bomb. Dimethyl maleate (0.06 mL, 0.5 mmol) in dichloromethane (6 mL) was added, the flask was sealed and the mixture was heated at 40° C. for 1.5 hours. The mixture was concentrated onto silica gel and purified by chromatography eluting on a gradient from 30% to 50% DCM in Hexanes. The residue was dried in vacuo over night to remove residual dimethyl maleate affording 72 mg of the title compound (87% yield).

trans-(4-methoxy-4-oxobutyl)-bis(trifluoromethyl)-1,3-Bis(2,6-diisopropylphenyl)-1,3-dihydro-2H-imidazol-2-ylidene-gold(III), S4

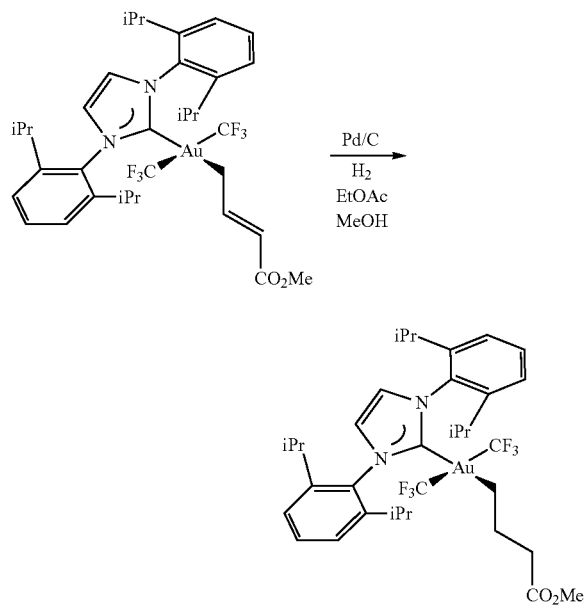

9 (288 mg, 0.35 mmol) was dissolved in a 1:1 mixture of ethyl acetate and methanol (35 mL). Pd/C (5 wt % palladium, 180 mg, 25 mol % loading) was added, and the mixture was degassed by sparging with $N_2$ for 5 minutes. A hydrogen balloon was then affixed to the flask and the solution was sparged for 5 minutes and then left under a static atmosphere of $H_2$. TLC analysis after 1.5 hours showed complete consumption of the starting material, and the $H_2$ was removed by sparging with $N_2$. The mixture was filtered through a pad of celite, and concentrated. The crude residue was purified by chromatography on silica gel eluting with 85:7.5:7.5 Hexanes/DCM/$Et_2O$, affording the title compound as a colorless solid (272 mg, 94% yield).

trans-(4-hydroxybutyl)-bis(trifluoromethyl)-1,3-Bis(2,6-diisopropylphenyl)-1,3-dihydro-2H-imidazol-2-ylidene-gold(III), S5

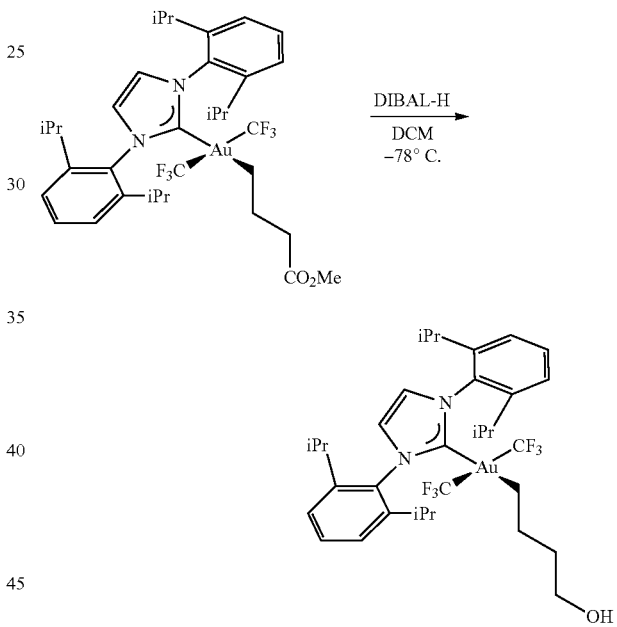

A solution of S4 (220 mg, 0.267 mmol) in DCM (16 mL) was cooled to −78° C. in a dry ice/acetone bath. A solution of DIBAL-H (1M in heptane, 1.35 mL, 5 equiv) was added dropwise, and the solution was stirred for 1 hour at −78° C. Saturated aqueous ammonium chloride (1 mL) was added in one portion and the mixture was warmed to room temperature, diluted with saturated aqueous Rochelle's salt, and stirred for 1 hour. The layers were separated, and the aqueous layer was extracted 2× with DCM. The combined organic layers were dried over $Na_2SO_4$, filtered and concentrated. It should be noted that in cases where residual aldehyde remained, the crude mixture was treated with sodium borohydride in methanol to achieve complete conversion. The crude mixture was purified by column chromatography on $SiO_2$ eluting with on a gradient from 8:1:1 to 6:2:2 Hexanes/DCM/$Et_2O$ affording the title compound as a colorless solid (191 mg, 90% yield).

17 trans-(4-((2-naphthoyl)oxy)butyl)-bis(trifluoromethyl)-1,3-Bis(2,6-diisopropylphenyl)-1,3-dihydro-2H-imidazol-2-ylidene-gold(III), 10

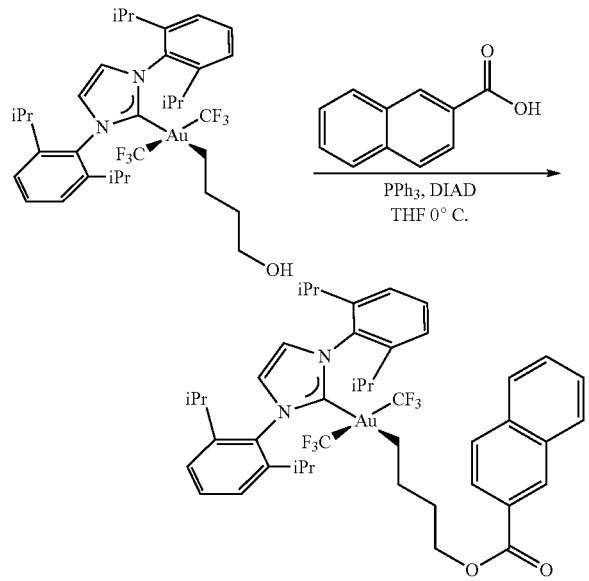

S5 (70 mg, 0.088 mmol), 2-naphthoic acid (15 mg, 1 equiv), and triphenylphosphine (35 mg, 1.5 equiv) were dissolved in dry THF (9 mL), and the mixture was cooled to 0° C. A solution of DIAD (27 mg, 1.5 equiv) in 1 mL of THF was added dropwise. The mixture was allowed to reach room temperature and stirred for 19 hours at which point a solution of brine was added. The layers were separated and the aqueous layer was extracted 3× with DCM. The combined organic layers were dried over MgSO$_4$, filtered, and concentrated. Column chromatography on SiO$_2$ eluting with 8:1:1 Hexanes/DCM/Et$_2$O afforded the desired product as a colorless solid (80 mg, 95% yield).

Bromo-(5-((2-naphthoyl)oxy)-1,1-difluoropentyl)-trifluoromethyl-1,3-Bis(2,6-diisopropylphenyl)-1,3-dihydro-2H-imidazol-2-ylidene-gold(III) (Mixture of Coordination Isomers), 19

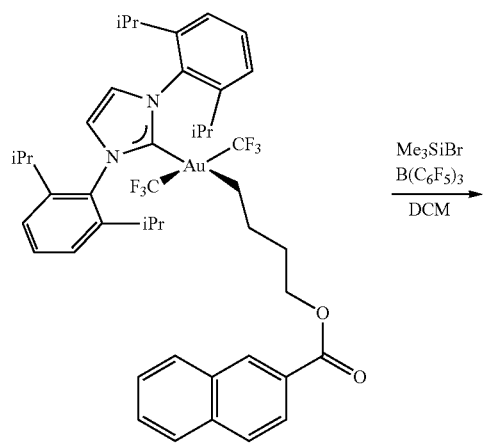

18

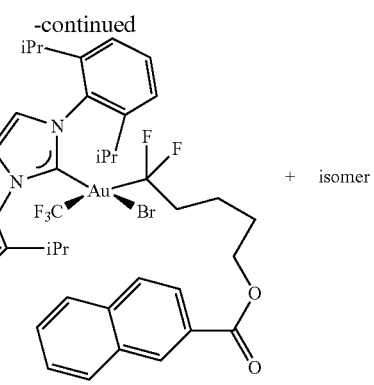

In a schlenk bomb, 10 (135 mg, 0.14 mmol) was dissolved in 6 mL of dichloromethane, and 0.19 mL (10 equiv) of TMSBr was added. A solution of B(C$_6$F$_5$)$_3$ (72 mg, 1 equiv) in dichloromethane (3 mL) was added and the mixture was monitored for consumption of the starting material using TLC. After 30 minutes the mixture was quenched with saturated aqueous bicarbonate solution, and the layers were separated. The aqueous layer was washed with DCM 2×, and the combined organics were dried over Na$_2$SO$_4$, filtered, and concentrated. Chromatography on SiO$_2$ eluting with 8:1:1 Hex/DCM/Et$_2$O afforded the title compound as a colorless solid (103 mg, 72% yield).

Acetato-(5-((2-naphthoyl)oxy)-1,1-difluoropentyl)-trifluoromethyl-1,3-Bis(2,6-diisopropylphenyl)-1,3-dihydro-2H-imidazol-2-ylidene-gold(III) (Mixture of Coordination Isomers), 22

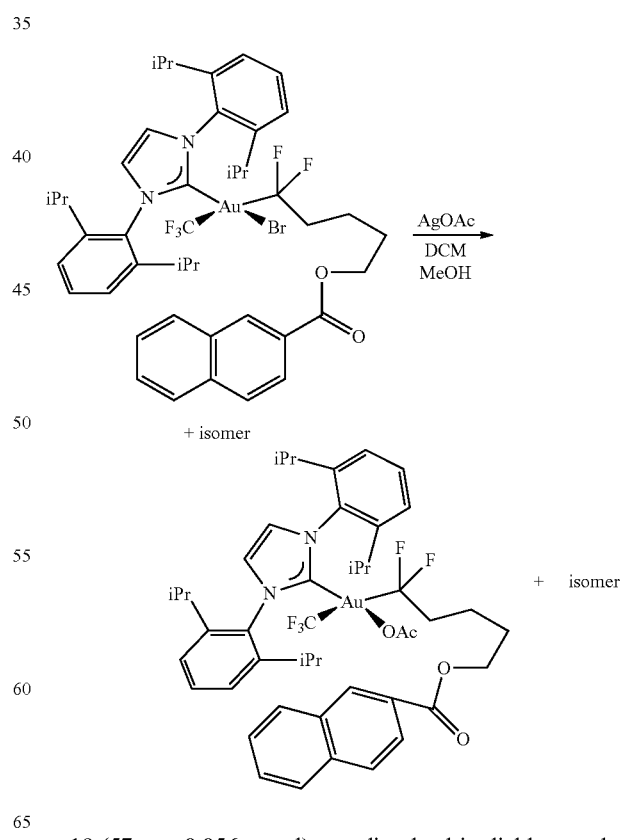

19 (57 mg, 0.056 mmol) was dissolved in dichloromethane (0.6 mL) and methanol (6 mL) and silver acetate (93 mg, 0.56 mmol, 10 equiv) was added. The mixture was sonicated briefly and stirred for 12 hours at room temperature in the dark. The mixture was filtered, and the filter cake was washed with dichloromethane. The combined filtrates were concentrated, and the residue was again extracted with dichloromethane, filtered and concentrated, affording the product as a colorless solid (50 mg). The resulting product was used as soon as possible without further purification. Storage, even at −20° C., results in the gradual reductive elimination of R—CF$_2$OAc.

trans-phenylbis(trifluoromethyl)-1,3-Bis(2,6-diisopropylphenyl)-1,3-dihydro-2H-imidazol-2-ylidene-gold(III), 12

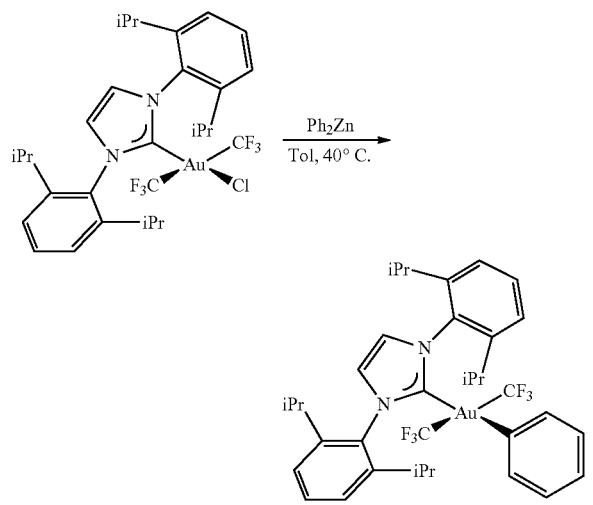

In a nitrogen filled glovebox, 5 (1.52 g, 2 mmol) and diphenyl zinc (1.1 g, 5 mmol, 2.5 equiv) were combined in a schlenk bomb and dissolved in toluene (125 mL). The flask was sealed with a teflon valve, removed from the glovebox and heated at 40° C. for 1.5 hours. Upon cooling, the mixture was quenched with H$_2$O and extracted three times with diethyl ether. The combined organic extracts were washed with brine, dried with sodium sulfate, filtered, and concentrated. The crude material was purified by silica gel chromatography eluting with 7:3 Hexanes/DCM yielding the title compound as a colorless solid (1.56 g, 97%).

trans-(4-aminophenyl)-bis(trifluoromethyl)-1,3-Bis(2,6-diisopropylphenyl)-1,3-dihydro-2H-imidazol-2-ylidene-gold(III), 13

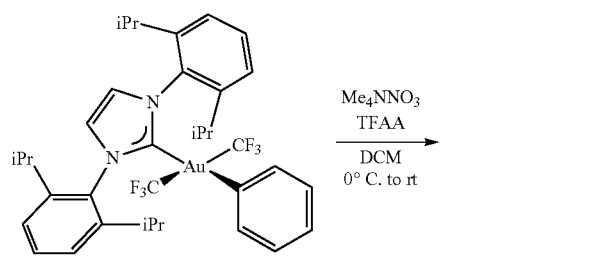

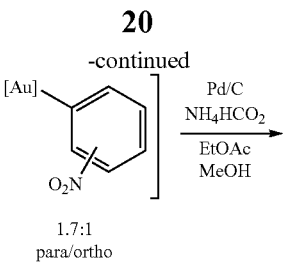

1.7:1 para/ortho

Stage 1: 12 (802 mg, 1 mmol) and tetramethylammonium nitrate (408 mg, 3 mmol, 3 equiv) were slurried in DCM (100 mL) and the mixture was cooled to 0° C. in an ice bath. Trifluoroacetic anhydride (0.70 mL, 5 mmol, 5 equiv) was added dropwise and the mixture was removed from the ice bath and allowed to warm to room temperature. The reaction was monitored by TLC for consumption of starting material. After 3 hours the mixture was quenched with saturated aqueous sodium bicarbonate and the layers were separated. The aqueous layer was extracted with dichloromethane and the combined organic layers were dried with MgSO$_4$, filtered and concentrated. The crude mixture was filtered through a short pad of silica with DCM, and the resulting mixture (1.7:1 para/ortho nitroaryl gold complex, 840 mg) was used without further purification.

Stage 2: The above crude product, ammonium formate (624 mg, 10 equiv) and 5% Pd/C (525 mg, 25% loading by Pd) were combined in a flask under N$_2$. Ethyl Acetate and Methanol (1:2, 45 mL total) were degassed by sparging and added to the solids with stirring. The mixture was monitored by TLC for the consumption of the para isomer of the nitroaryl gold complex. After 2 hours, the mixture was filtered through a pad of celite with ethyl acetate and concentrated. The crude mixture was extracted with dichloromethane, the insoluble solids were filtered off, and DCM extract was concentrated onto silica gel. This was dry-loaded onto a column and purified by chromatography eluting on a gradient from 8:1:1 to 10:5:5 (Hexanes/DCM/Et$_2$O) to afford the title compound as a colorless solid (390 mg, 48% yield over 2 steps), as well as 170 mg of unreacted ortho-nitro complex (20%).

trans-(4-(5-methylisoxazole-4-carboxamido)phenyl)-bis(trifluoromethyl)-1,3-Bis(2,6-diisopropylphenyl)-1,3-dihydro-2H-imidazol-2-ylidene-gold(III), 14

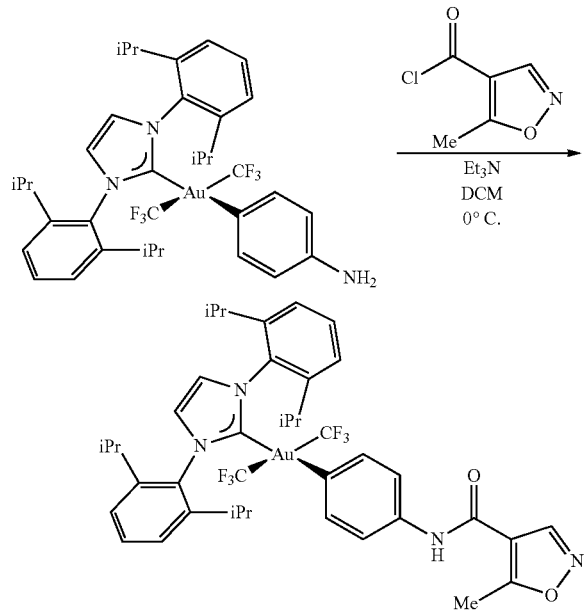

13 (160 mg, 0.2 mmol) and triethylamine (80 μL, 3 equiv) were dissolved in DCM (2 mL) and the mixture was cooled to 0° C. in an ice bath. 5-methylisoxazole-4-carbonyl chloride (prepared from the commercially available acid by treatment with oxalyl chloride and catalytic DMF) in dichloromethane (2 mL) was added dropwise, resulting in a gradual color change from pale yellow to dark purple. The reaction was monitored by TLC for consumption of starting material while maintaining the temperature at 0° C. After 1 hour the mixture was quenched with saturated aqueous sodium bicarbonate and the layers were separated. The aqueous layer was extracted with dichloromethane and the combined organic layers were dried with $Na_2SO_4$, filtered and concentrated. The crude mixture was purified by silica gel chromatography eluting on a gradient from 30:5:5 to 6:2:2 (Hex/DCM/$Et_2O$) affording the desired product as a pale yellow solid (142 mg, 76% yield).

trans-(3-hydroxypropyl)-bis(trifluoromethyl)-1,3-Bis(2,6-diisopropylphenyl)-1,3-dihydro-2H-imidazol-2-ylidene-gold(III), S6

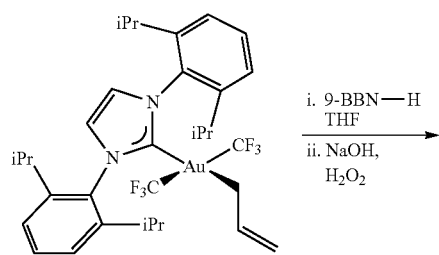

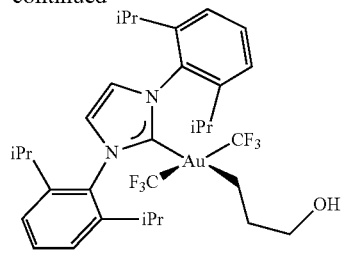

In a nitrogen filled glovebox, 6 (382 mg, 0.5 mmol) and solid 9-borabicyclo[3.3.1]nonane (64 mg, 0.525 mmol, 1.05 equiv) were dissolved in THF (25 mL total) and combined in a round bottom flask. The flask was sealed with a rubber septum, brought out of the box and stirred for 12 hours under an $N_2$ atmosphere on a Schlenk line. 5 mL of 1M aqueous NaOH followed by 5 mL of 35% aqueous hydrogen peroxide were injected and the mixture was stirred for an additional hour. The mixture was diluted with water and extracted 3× with dichloromethane. The combined organic extracts were dried with sodium sulfate, filtered, and concentrated. The crude residue was purified by column chromatography eluting with 3:1:1 Hexanes/DCM/$Et_2O$ affording the desired product as a colorless solid (290 mg, 74% yield).

trans-(3-iodopropyl)-bis(trifluoromethyl)-1,3-Bis(2,6-diisopropylphenyl)-1,3-dihydro-2H-imidazol-2-ylidene-gold(III), 15

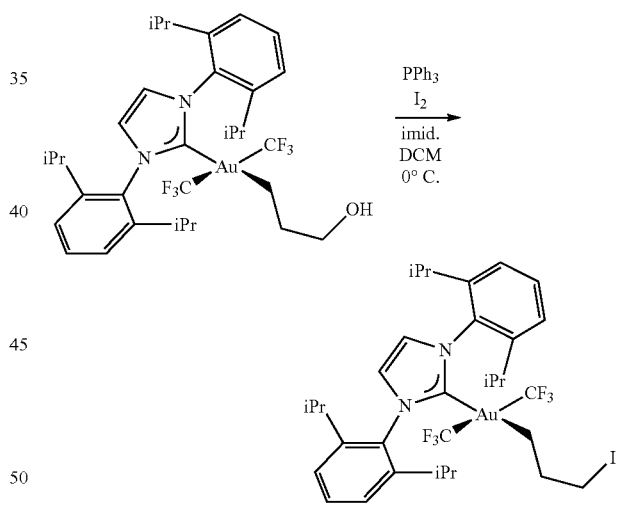

Triphenylphosphine (291 mg, 1.11 mmol, 3 equiv) and imidazole (76 mg, 1.11 mmol, 3 equiv) were dissolved in DCM (12 mL) and cooled to 0° C. in an ice bath. Solid iodine (282 mg, 1.11 mmol, 3 equiv) was added and stirred 15 minutes resulting in a yellow-orange solution. S6 (290 mg, 0.37 mmol) in DCM (6 mL) was added slowly and the mixture was removed from the ice bath and allowed to warm to room temperature. After 20 minutes TLC showed complete consumption of the starting material. The mixture was filtered, washing the insoluble material with additional DCM and concentrated directly onto silica which was dry loaded onto a column and purified by chromatography eluting with 5:1:1 Hex/DCM/$Et_2O$. The resulting product was washed with cold hexanes to remove residual co-eluting $PPh_3$, to afford the title compound as a colorless solid (280 mg, 85% yield).

trans-3-(acetylthio)propyl)(1,3-bis(2,6-diisopropylphenyl)-1,3-dihydro-2H-imidazol-2-ylidene)bis(trifluoromethyl)gold(III), S7

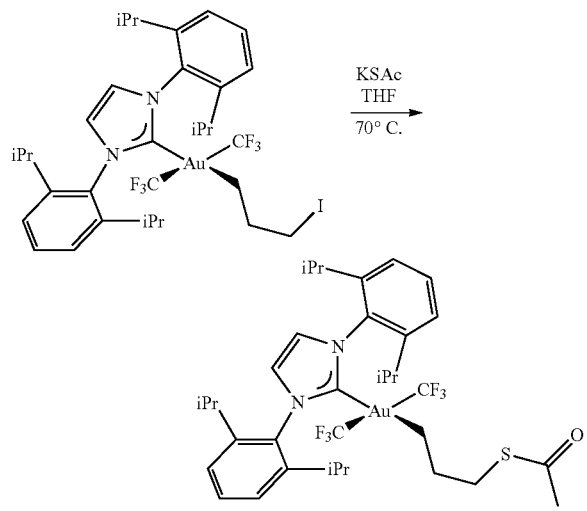

15 (280 mg, 0.313 mmol) and potassium thioacetate (40 mg, 1.1 equiv) were combined in a Schlenk bomb and dissolved in THF (7 mL). The mixture was degassed by sparging with $N_2$, sealed with a teflon valve and heated at 70° C. for 12 hours. Upon cooling, the mixture was filtered, washing the filter cake with diethyl ether, and concentrated directly onto silica which was dry loaded onto a column and purified by chromatography eluting on a gradient (18:1:1 to 8:1:1 Hex/DCM/Et$_2$O) to afford the title compound as a yellow solid (217 mg, 82% yield).

trans-(3-(chlorosulfonyl)propyl)-bis(trifluoromethyl)-1,3-Bis(2,6-diisopropylphenyl)-1,3-dihydro-2H-imidazol-2-ylidene-gold(III), 16

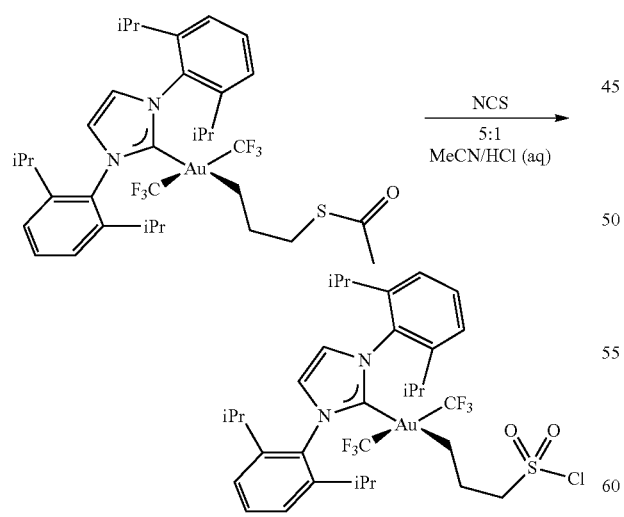

S7 (226 mg, 0.27 mmol) was dissolved in 13.5 mL of acetonitrile, and 2.7 mL of 2M aqueous HCl was added, followed by N-Chlorosuccinimide (144 mg, 4 equiv). The mixture was stirred under air for 1 hour at which time TLC showed consumption of the starting material. The reaction mixture was diluted with diethyl ether and water, and the layers were separated. The aqueous layer was extracted 2× with diethyl ether, and the combined organic fractions were again washed with water before drying with sodium sulfate, filtration, and concentration. Column Chromatography on silica gel eluting with 85:7.5:7.5 Hex/DCM/Et$_2$O afforded the title compound as a colorless solid (203 mg, 87% yield).

trans-(1,3-bis(2,6-diisopropylphenyl)-1,3-dihydro-2H-imidazol-2-ylidene)(3-((3-(2-cyano-3-(trifluoromethyl)phenoxy)phenoxy)sulfonyl)propyl)bis(trifluoromethyl)gold, 17

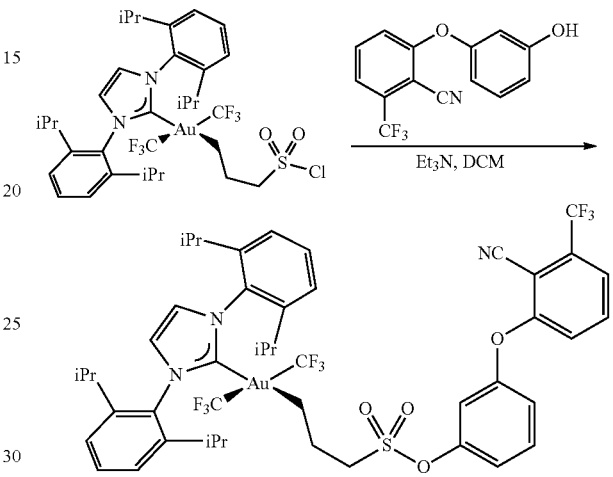

16 (170 mg, 0.196 mmol), in dichloromethane (10 mL) was added to a solution of 2-(3-hydroxyphenoxy)-6-(trifluoromethyl)benzonitrile (57 mg, 1.05 equiv) and trimethylamine (40 µL, 1.5 equiv) in dichloromethane (10 mL). The solution was stirred for 25 minutes at which point the TLC showed complete consumption of the starting material. Chromatography on silica gel eluting on a gradient from 8:1:1 to 7:1.5:1.5 Hexanes/DCM/Et$_2$O afforded the title compound as a colorless solid (184 mg, 85% yield).

Bromo-(4-((3-(2-cyano-3-(trifluoromethyl)phenoxy)phenoxy)sulfonyl)-1,1-difluorobutyl)-trifluoromethyl-1,3-Bis(2,6-diisopropylphenyl)-1,3-dihydro-2H-imidazol-2-ylidene-gold(III) (Mixture of Coordination Isomers), 20

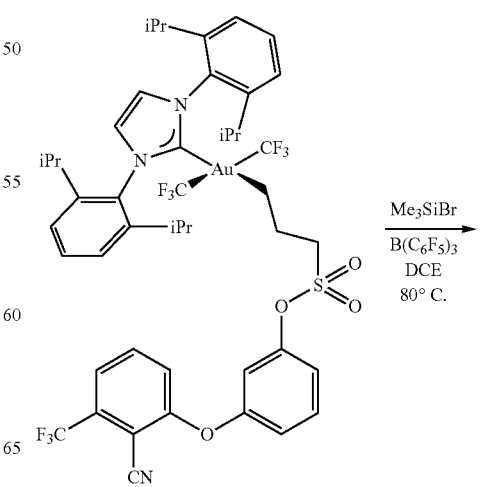

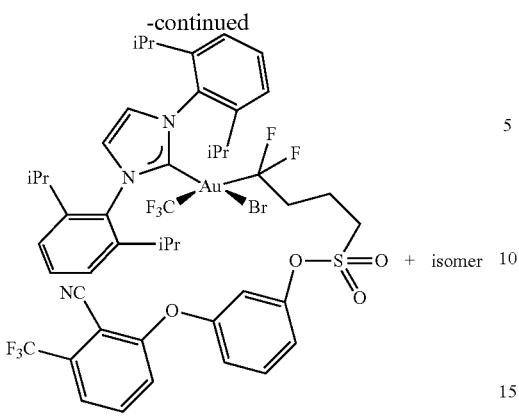

+ isomer

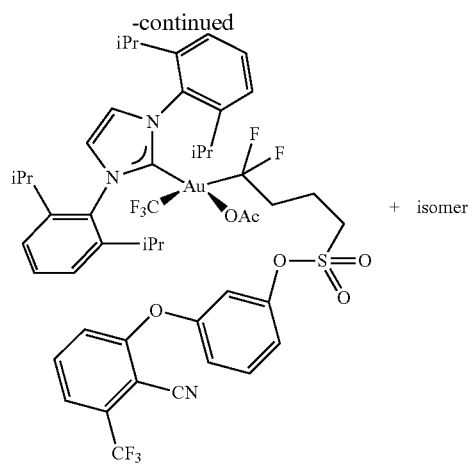

+ isomer

In a schlenk bomb, 17 (116 mg, 0.104 mmol) was dissolved in 3 mL of DCE, and TMSBr (0.14 mL, 10 equiv) followed by a solution of 2 (53 mg, 1 equiv) in 3 mL of DCE. The flask was sealed with a Teflon valve and the solution was heated to 80° C. and monitored by TLC for consumption of the starting material. After 1 hour, the solution was cooled to room temperature and quenched with aqueous sodium bicarbonate. The layers were separated, the aqueous layer was extracted with DCM, and the combined organic layers were dried over $Na_2SO_4$, filtered, and concentrated.

Purification by column chromatography on silica (7:1.5:1.5 Hex/DCM/$Et_2O$ eluent) afforded the product as a colorless solid, which was further purified by precipitation from diethyl ether with hexanes (60 mg, 55% yield).

20 (60 mg, 0.051 mmol) was dissolved in a mixture of 0.6 mL of dichloromethane and 6 mL of methanol, and 85 mg (10 equiv) of silver acetate was added. The mixture was stirred vigorously overnight at room temperature in the dark. The resulting mixture was filtered, concentrated, extracted with DCM, filtered again, and concentrated (56 mg, colorless solid). The resulting product was used as soon as possible without further purification. Storage, even at −20° C., results in the gradual reductive elimination of R—$CF_2OAc$.

trans-(cyclopropylmethyl)-bis(trifluoromethyl)-1,3-Bis(2,6-diisopropylphenyl)-1,3-dihydro-2H-imidazol-2-ylidene-gold(III), S8

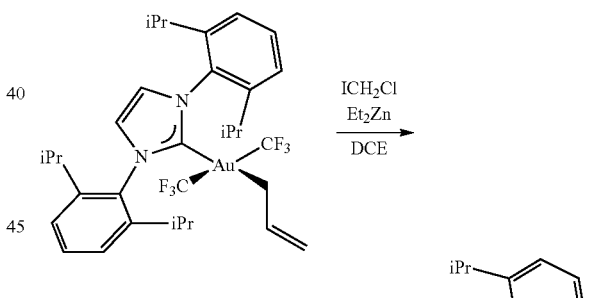

Acetato-(4-((3-(2-cyano-3-(trifluoromethyl)phenoxy)phenoxy)sulfonyl)-1,1-difluorobutyl)-trifluoromethyl-1,3-Bis(2,6-diisopropylphenyl)-1,3-dihydro-2H-imidazol-2-ylidene-gold(III) (Mixture of Coordination Isomers), 23

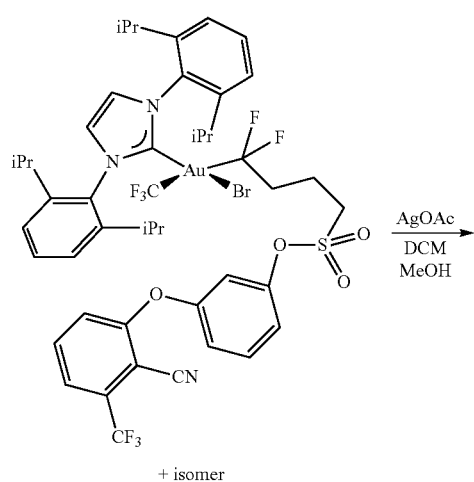

+ isomer

Figure 13:
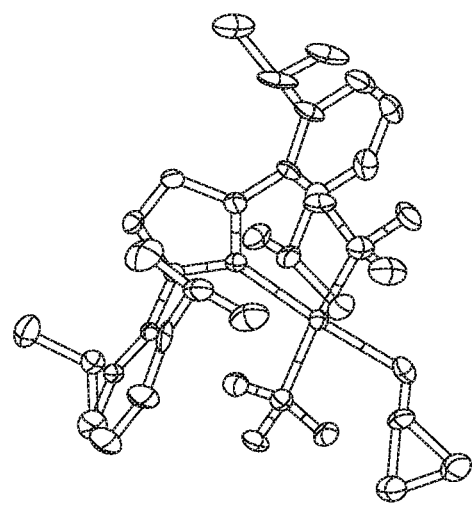
FIG. 13 illustrates an example three dimensional molecule model of trans-(cyclopropylmethyl)-bis(trifluoromethyl)-1,3-Bis(2,6-diisopropylphenyl)-1,3-dihydro-2H-imidazol-2-ylidene-gold(III)
Figure 14:
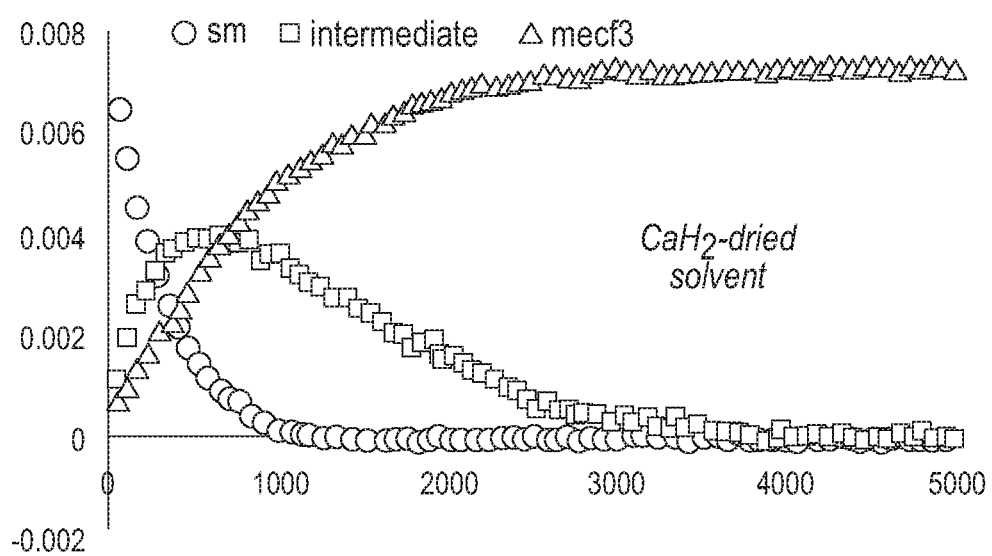
FIG. 14 illustrates graphical data for concentrations of intermediate compounds observed using a first drying method.
Figure 15:
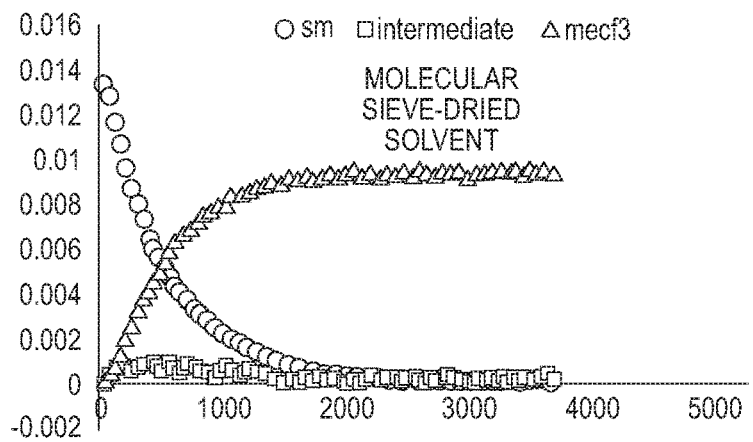
FIG. 15 illustrates graphical data for concentrations of intermediate compounds observed using a second drying method.
Figure 16:
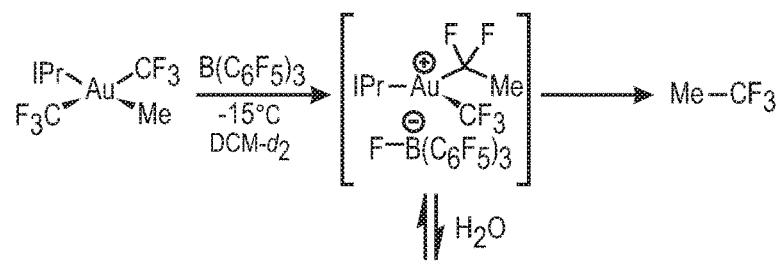
FIG. 16 illustrates an example first order decay based on the graphical data illustrated in FIG. 15.
Figure 16:
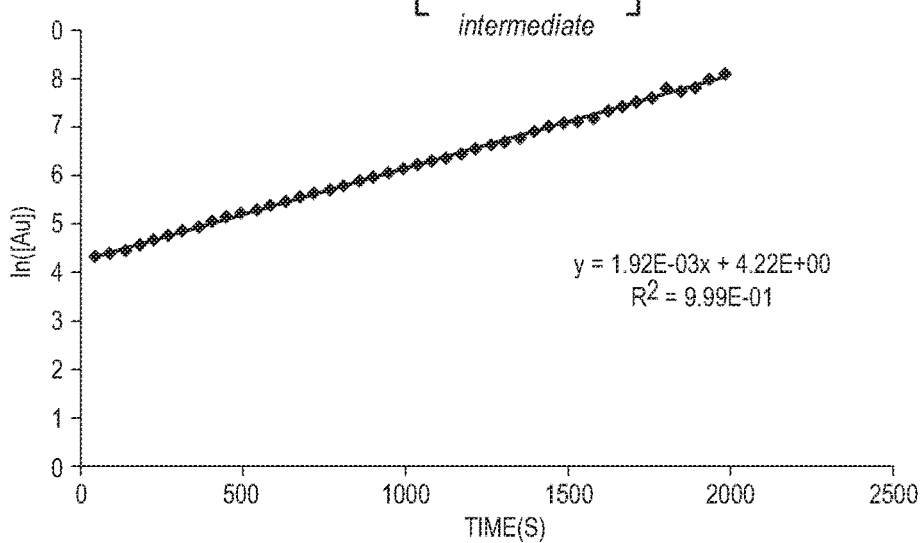
Figure 17:
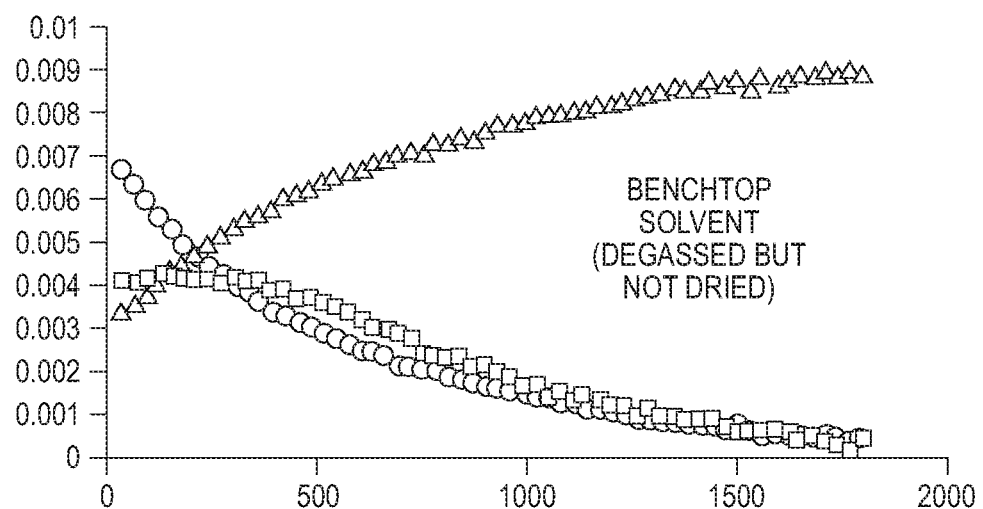
FIG. 17 illustrates graphical data for concentrations of intermediate compounds observed using a first drying method.
Figure 18:
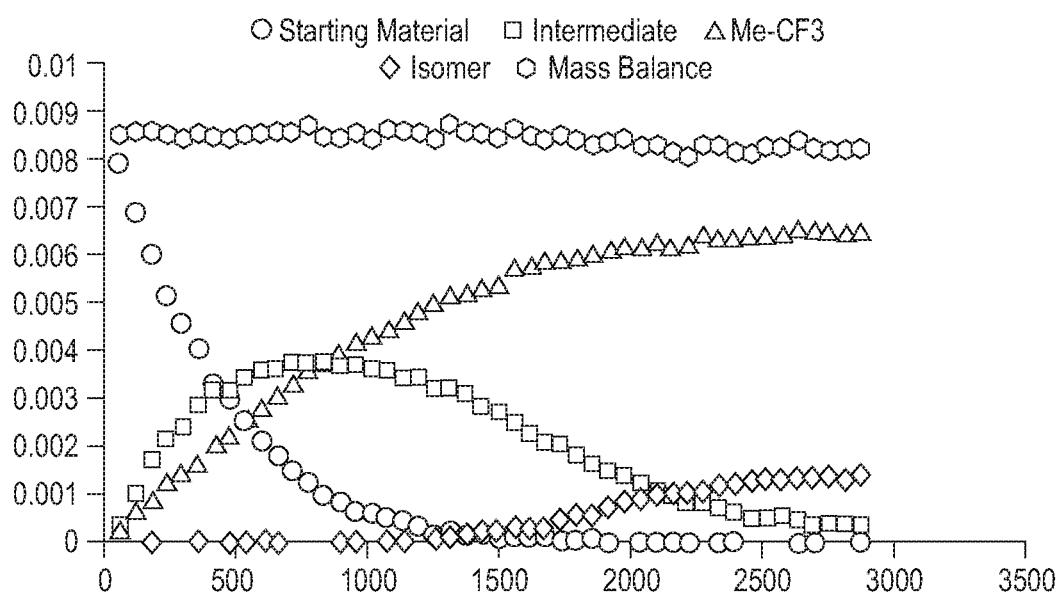
FIG. 18 illustrates graphical data for concentrations of intermediate compounds observed over time including isomer formation.

In a nitrogen filled glovebox, 6 (76 mg, 0.1 mmol) and diethyl zinc (0.2 mL of 1M hexanes solution, 2 equiv) were dissolved in DCE (3 mL) in a round bottom flask. Chloroiodomethane (71 mg, 4 equiv) in 3 mL of DCE was added and the mixture was sealed with a rubber septum, brought out of the box and stirred for 1 hour under an $N_2$ atmosphere on a Schlenk line. 5 mL of $H_2O$ were injected and the mixture was extracted 3× with diethyl ether. The combined organic extracts were dried with sodium sulfate, filtered, and concentrated. The crude residue was purified by column chromatography eluting with 1:1 Hexanes/DCM affording the desired product as a colorless solid (69 mg, 88% yield). A three dimensional molecule model is illustrated in FIG. 13.

trans-(2,3-dihydroxypropyl)-bis(trifluoromethyl)-1,3-Bis(2,6-diisopropylphenyl)-1,3-dihydro-2H-imidazol-2-ylidene-gold(III), S9

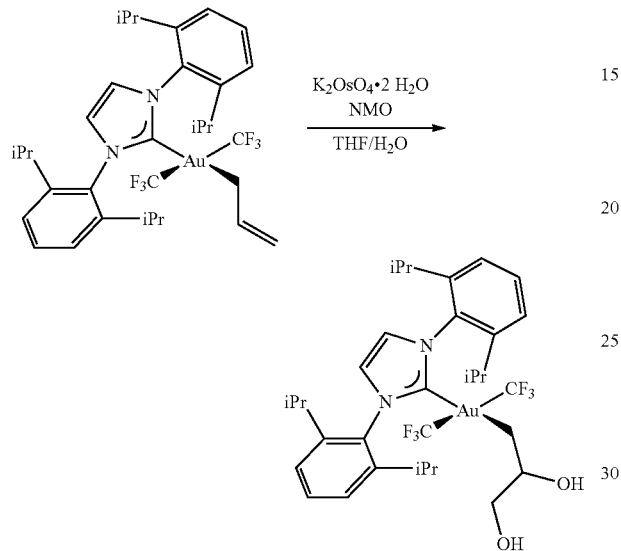

6 (110 mg, 0.144 mmol) and potassium osmate dihydrate (1 mg, 0.02 equiv) were dissolved in 1:1 THF/H$_2$O (6 mL) in a round bottom flask. N-methylmorpholine-N-oxide (34 mg, 2 equiv) was added, and additional THF~1 mL was added to solubilize the gold complex. The mixture was stirred for 12 hours under air, then 5 mL of 1M aqueous sodium bisulfate was added, and the mixture was extracted 3× with diethyl ether. The combined organic extracts were dried with sodium sulfate, filtered, and concentrated. The crude residue was purified by column chromatography eluting with 3:1:1 Hexanes/DCM/Et$_2$O affording the desired product as a colorless solid (80 mg, 70% yield).

trans-(2-oxoethyl)-bis(trifluoromethyl)-1,3-Bis(2,6-diisopropylphenyl)-1,3-dihydro-2H-imidazol-2-ylidene-gold(III), S9

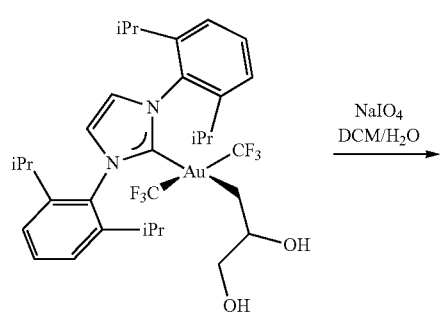

6 (75 mg, 0.095 mmol) and sodium periodate (100 mg, 5 equiv) were dissolved in 4:1 DCM/H$_2$O (2.5 mL). The mixture was vigorously stirred for 18 hours under air, diluted with DCM and washed 3× with brine. The organic layer was dried with sodium sulfate, filtered, and concentrated. The crude residue was purified by column chromatography eluting with 85:7.5:7.5 Hexanes/DCM/Et$_2$O affording the desired product as a colorless solid (36 mg, 50% yield).

trans-ethyl-bis(trifluoromethyl)-1,3-Bis(2,6-diisopropylphenyl)-1,3-dihydro-2H-imidazol-2-ylidene-gold (III), S10

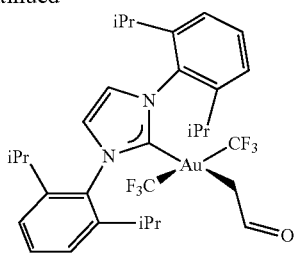

In a schlenk bomb, 5 (76 mg, 0.1 mmol) was dissolved in THF (10 mL) and a solution of 1.1M Et$_2$Zn in hexanes was added (1.8 mL, 20 equiv). The flask was sealed with a Teflon needle valve and the mixture was heated at 60° C. for 12 hours. Upon cooling, the mixture was quenched carefully with water and extracted 3× with diethyl ether. The organic layer was dried with sodium sulfate, filtered, and concentrated. The crude residue was purified by column chromatography eluting with 6:4 Hexanes/DCM affording the desired product as a colorless solid (47 mg, 62% yield).

trans-phenylethynyl-bis(trifluoromethyl)-1,3-Bis(2,
6-diisopropylphenyl)-1,3-dihydro-2H-imidazol-2-
ylidene-gold(III), S11

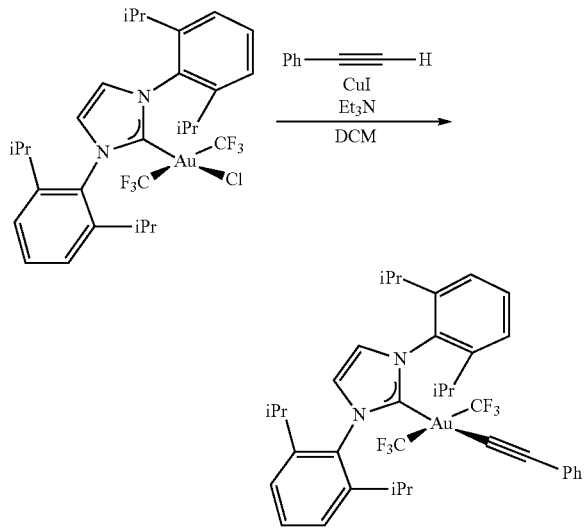

In a flame-dried round-bottom flask under $N_2$, 5 (76 mg, 0.1 mmol) was dissolved in 9 mL of DCM. In a separate flame-dried round-bottom flask under $N_2$, CuI (8 mg, 0.04 mmol, 4 equiv) was slurried in DCM (1 mL) and phenylacetylene (0.07 mL, 6 equiv) and trimethylamine (1 mL, 70 equiv) was added and stirred until the mixture turned yellow. This latter solution was transferred via syringe to the [Au] solution and the mixture was stirred at room temperature for 15 hours at which point TLC indicated complete conversion. The mixture was directly concentrated onto silica gel and purified by column chromatography eluting on a gradient from 6:1 to 2:1 Hexanes/DCM to afford the product as a colorless solid (78 mg, 93%).

Reductive Elimination of Trifluoroethane (Catalytic Borane)

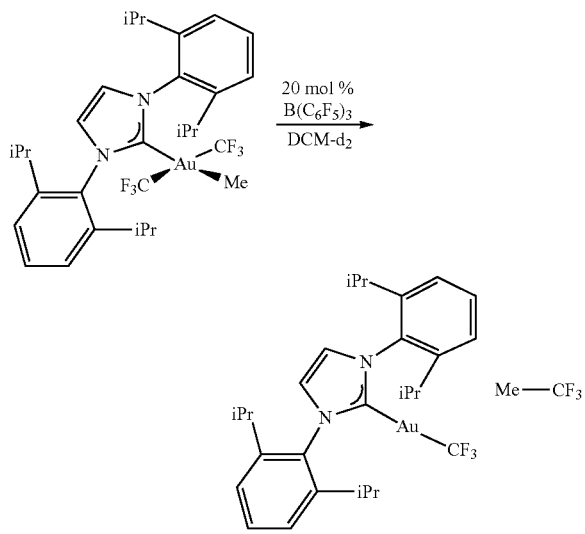

In a nitrogen-filled glovebox, to a solution of 1a (7.4 mg, 0.01 mmol) in DCM-$d_2$ (0.3 mL) in a silylated NMR tube was added a solution of tris(pentafluorophenylborane) in DCM-$d_2$ (1 mg, 0.002 mmol, in 0.3 mL, prepared a stock solution). The mixture was capped with an NMR-tube septum and sealed with electrical tape. Analysis by FNMR after 5 minutes showed the complete consumption of 1, formation of Me-$CF_3$ as the major product, along with $C_6F_5H$, and IPr—Au—$CF_3$ as the major Au-containing product.

Reductive Elimination of Trifluoroethane (Stoichiometric Borane)

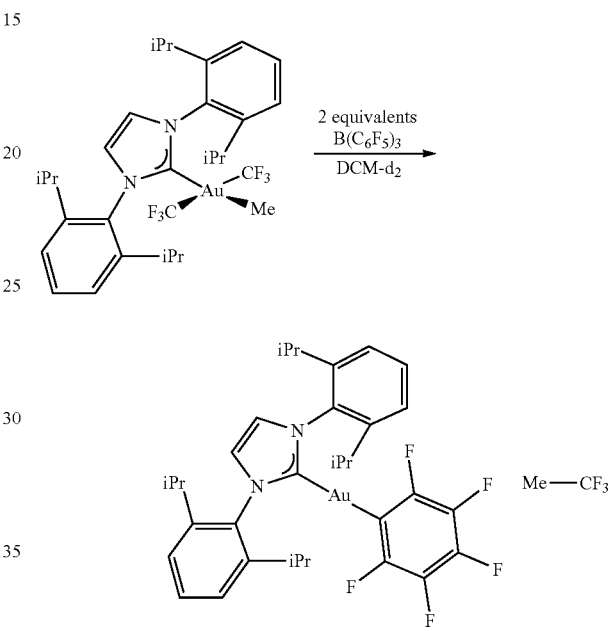

In a nitrogen-filled glovebox, to a solution of 1a (7.4 mg, 0.01 mmol) in DCM-$d_2$ (0.3 mL) in a silylated NMR tube was added a solution of tris(pentafluorophenylborane) in DCM-$d_2$ (10.2 mg, 0.02 mmol, in 0.3 mL). The mixture was capped with an NMR-tube septum and sealed with electrical tape. Analysis by FNMR after 5 minutes showed the complete consumption of 1, formation of Me-$CF_3$ as the major product, along with $C_6F_5H$, and IPr—Au—$C_6F_5$ as the exclusive Au-containing product.

Reductive Elimination of Trifluoroethane (Stoichiometric Borane with Alkene Trap)

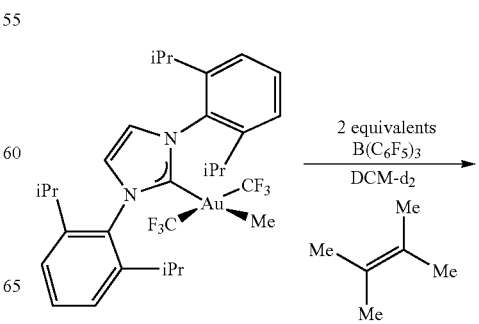

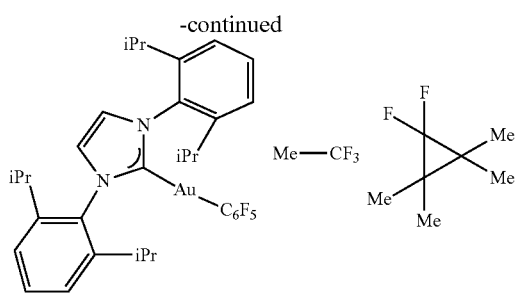

In a nitrogen-filled glovebox, to a solution of 1a (7.4 mg, 0.01 mmol) and tetramethylethylene (1.6 mg, 0.02 mmol, prepared as a stock solution) in DCM-$d_2$ (0.3 mL) in a silylated NMR tube was added a solution of tris(pentafluorophenylborane) in DCM-$d_2$ (10.2 mg, 0.02 mmol, in 0.3 mL). The mixture was capped with an NMR-tube septum and sealed with electrical tape. Analysis by FNMR after 5 minutes showed the complete consumption of 1, formation of Me-$CF_3$ as the major product, along with $C_6F_5H$, 1,1,2,2-dimethyl-3,3-difluorocyclopropane, and IPr—Au—$C_6F_5$ as the exclusive Au-containing product. GC-MS analysis of the mixture also indicated the presence of the difluorocyclopropane product (m/z=41, 119, and 134, consistent with literature spectrum).

Reductive Elimination of Difluoroethyltriflate (Stoichiometric TMSOTf)

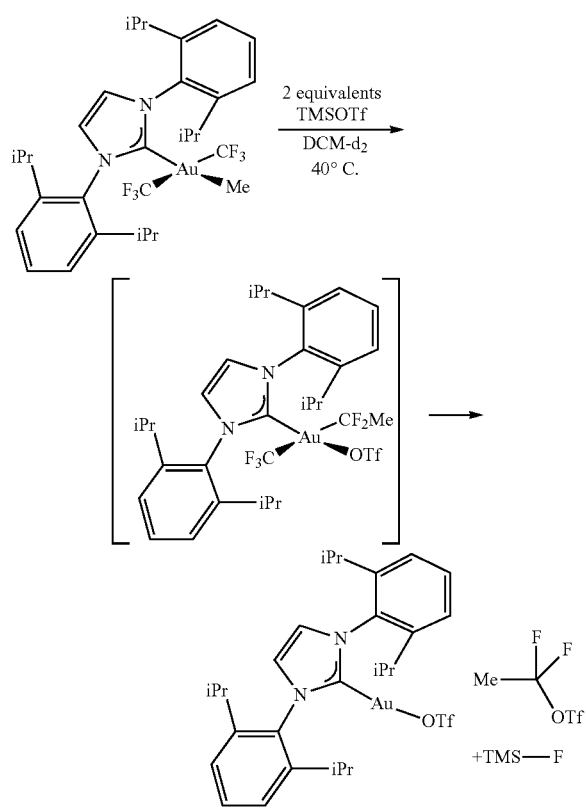

In a nitrogen filled glovebox, 1a (7.4 mg, 0.01 mmol) was dissolved in DCM-$d_2$ (0.3 mL) in a silylated NMR tube and a solution of TMSOTf (4.4 mg, 2 equiv) in DCM-$d_2$ (0.3 mL) was added. The solution was capped with a rubber septum and heated at 40° C. Conversion was monitored by FNMR, indicating the formation of MeCF$_2$OTf {F NMR (376 MHz, Methylene Chloride-$d_2$) δ -57.59 (qq, J=14.7, 5.6 Hz, 2F), -74.11 (d, J=5.6 Hz, 3F)}[31], along with IPrAuOTf and TMSF. An intermediate was also detected and assigned as the difluoroethyl Au(III) triflate shown above by analogy to 4 {$^{19}$F NMR (376 MHz, Methylene Chloride-$d_2$) δ -34.51 (t, J=11.9 Hz, 3F), -61.14--61.50 (m, 2F), -71.04 (s, 3F)}. (48)

Reductive Elimination of Trifluoroethane (Silver Mediated from 4)

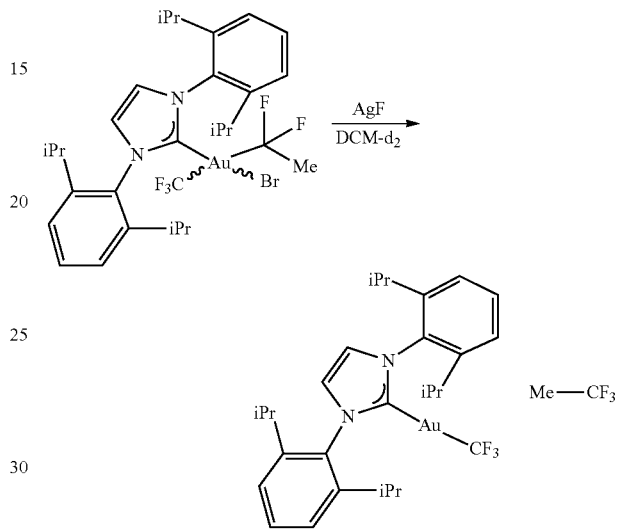

4 (39 mg, 0.05 mmol) was dissolved in DCM-$d_2$ (1 mL), and silver fluoride was added (64 mg, 10 equiv). The mixture was sonicated briefly and stirred vigorously for 12 hours in the dark. The mixture was filtered directly into an NMR tube, and an additional 64 mg (10 equiv) of AgF was added. The tube was sealed with a rubber septum and sonicated for an additional 20 minutes. The mixture was allowed to stand with occasional agitation for an additional 24 hours, with NMR spectra recorded periodically. These indicated the formation of two isomers of an intermediate Au(III)-fluoride which is observable, as well as another unidentified Au(III) product. The majority of the material is observed to convert to IPrAuCF$_3$ and MeCF$_3$, with a small amount of 1,1-difluoroethylene formed as a byproduct. After 36 hours, the starting complex was consumed, with 32% conversion to IPrAuCF$_3$ observed, the remainder of the mass balance taken up by the Au(III)-F and unidentified Au(III) species. For ease of interpretation, the X-axis has been segmented to show relevant peaks.

Reductive Elimination of Trifluoroethane (PCy$_3$; Catalytic Borane)

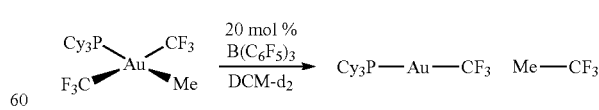

In a nitrogen-filled glovebox, to a solution of 1 b (6.1 mg, 0.01 mmol) in DCM-$d_2$ (0.3 mL) in a silylated NMR tube was added a solution of tris(pentafluorophenylborane) in DCM-$d_2$ (1 mg, 0.002 mmol, in 0.3 mL, prepared a stock solution). The mixture was capped with an NMR-tube septum and sealed with electrical tape. Analysis by FNMR after 5 minutes showed the complete consumption of 1, formation of Me-CF$_3$ as the major product, along with Cy$_3$P—Au—CF$_3$ as the major Au-containing product.

Reductive Elimination of Trifluoroethane (Stoichiometric Borane)

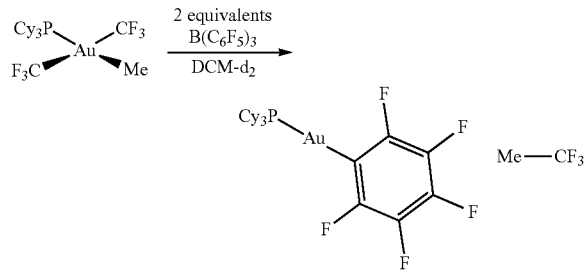

In a nitrogen-filled glovebox, to a solution of 1 b (6.1 mg, 0.01 mmol) in DCM-d$_2$ (0.3 mL) in a silylated NMR tube was added a solution of tris(pentafluorophenylborane) in DCM-d$_2$ (10.2 mg, 0.02 mmol, in 0.3 mL). The mixture was capped with an NMR-tube septum and sealed with electrical tape. Analysis by FNMR after 5 minutes showed the complete consumption of 1, formation of Me-CF$_3$ as the major product, along with C$_6$F$_5$H, and IPr—Au—C$_6$F$_5$ as the exclusive Au-containing product.

Reductive Elimination of Trifluorotoluene (Stoichiometric Borane)

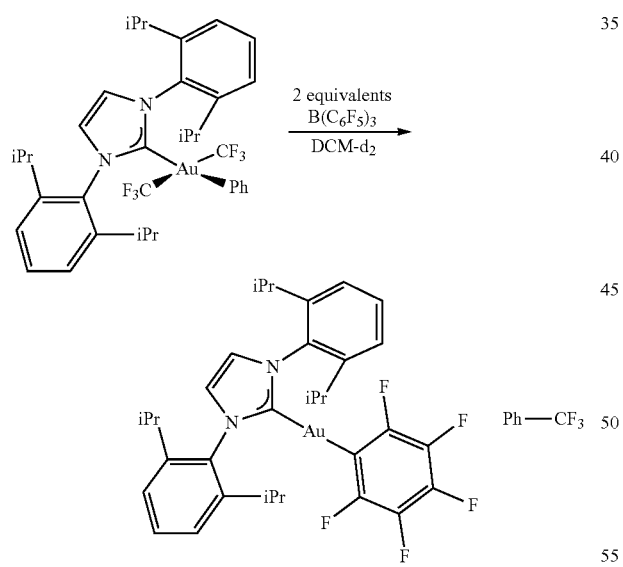

In a nitrogen-filled glovebox, to a solution of 12 (8 mg, 0.01 mmol) in DCM-d$_2$ (0.3 mL) in a silylated NMR tube was added a solution of tris(pentafluorophenylborane) in DCM-d$_2$ (10.2 mg, 0.02 mmol, in 0.3 mL). The mixture was capped with an NMR-tube septum and sealed with electrical tape. Analysis by FNMR after 5 minutes showed the almost complete consumption of 12, formation of Ph-CF$_3$ as the major product, along with C$_6$F$_5$H, and IPr—Au—C$_6$F$_5$ as the major Au-containing product.

Reductive Elimination of Bromodifluorotoluene (Catalytic Borane)

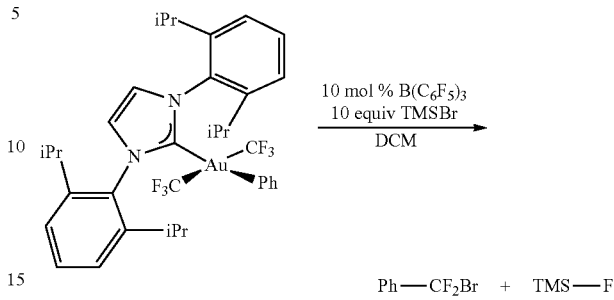

In a nitrogen-filled glovebox, to a solution of 12 (7.4 mg, 0.01 mmol) in DCM (0.3 mL) in a silylated NMR tube was added TMS-Br (0.01 mL, 10 equiv) followed by a solution of tris(pentafluorophenylborane) in DCM (0.5 mg, 0.001 mmol, in 0.3 mL). The mixture was capped with an NMR-tube septum and sealed with electrical tape. Analysis by FNMR after 1 hour showed ~15% conversion to afford a mixture of PhCF$_2$Br and TMS-F. Peaks for 2 are too small to be seen at this scale.

Reductive Elimination of 1-(4-(4,4,4-trifluorobutyl)phenyl)ethan-1-one (Stoichiometric Borane)

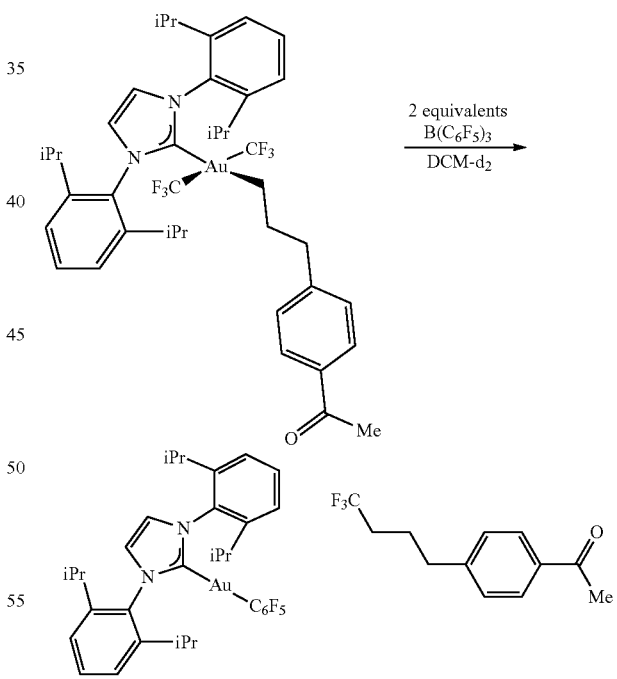

In a nitrogen filled glovebox, to a solution of 7 (66 mg, 0.075 mmol) in 2 mL of DCM was added a solution of B(C$_6$F$_5$)$_3$ (77 mg, 0.15 mmol) in 2 mL of DCM. An immediate color change to pale yellow occurred, and the mixture was capped with a septum cap, and brought out of the glovebox.

After 10 minutes, TLC analysis indicated complete consumption of the starting material, and a solution of saturated aqueous sodium bicarbonate was injected through the septum, and the mixture was vigorously stirred for 10 minutes. The solution was diluted with water and dichloromethane. The organic layer was separated and the aqueous layer was washed 2× with DCM. The combined organic layers were dried over $Na_2SO_4$, filtered, and concentrated. The crude residue was purified by column chromatography eluting with (18:1:1 Hexanes/DCM/$Et_2O$) to afford the title compound (12 mg, 70% yield).

When conducted in an NMR tube on 0.005 mmol scale, 97% yield by FNMR was observed.

Reductive Elimination of 5,5,5-trifluoropentyl 2-naphthoate (Stoichiometric Borane)

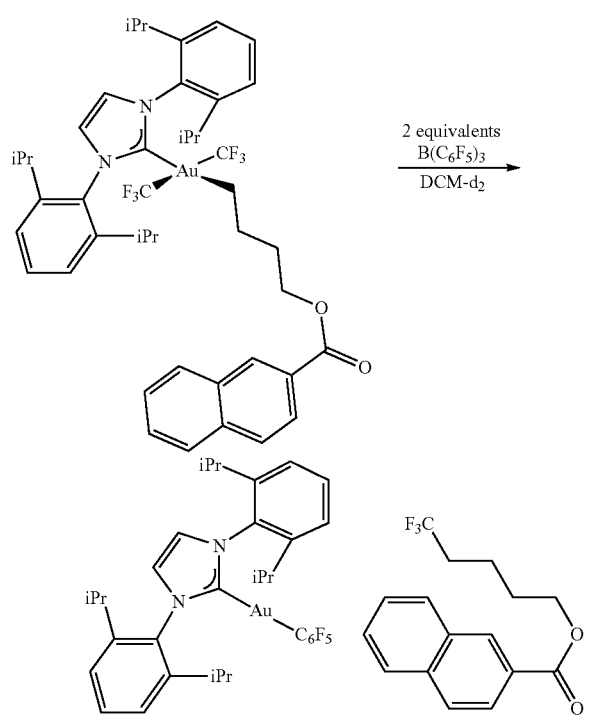

In a nitrogen filled glovebox, to a solution of 10 (54 mg, 0.058 mmol) in 2 mL of DCM was added a solution of $B(C_6F_5)_3$ (59 mg, 0.116 mmol) in 2 mL of DCM. An immediate color change to orange occurred, and the mixture was capped with a septum cap and brought out of the glovebox. TLC analysis after 45 minutes indicated complete consumption of the starting material.

A solution of saturated aqueous sodium bicarbonate was injected through the septum, and the mixture was vigorously shaken. The septum was removed and the solution was diluted with water and dichloromethane. The organic layer was separated and the aqueous layer was washed 2× with DCM. The combined organic layers were dried over $MgSO_4$, filtered, and concentrated. The crude residue was purified by silica gel chromatography (97:3 Hexanes/$Et_2O$). The resulting residue was extracted with cold hexanes to remove the desired product from co-eluting $IPrAuC_6F_5$ (12 mg, 60%).

When conducted in an NMR tube on 0.005 mmol scale, 80% yield by FNMR was observed.

Reductive Elimination of Leflunomide (Stoichiometric Borane)

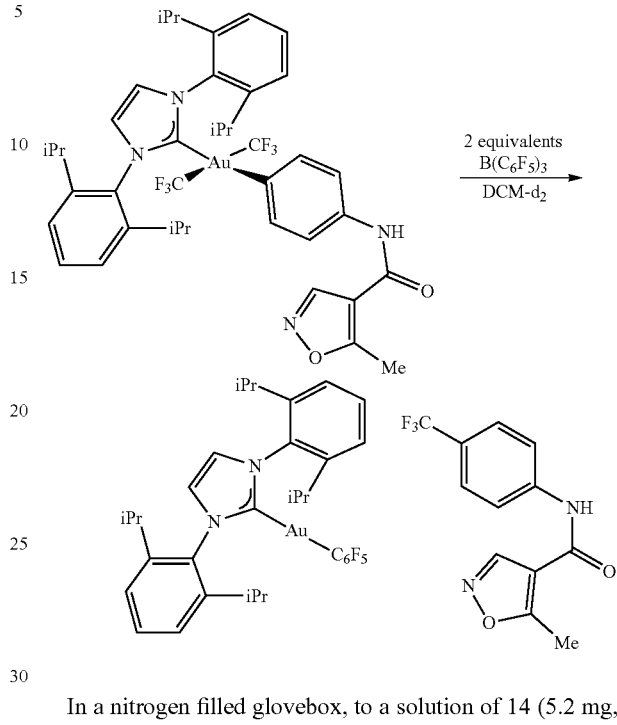

In a nitrogen filled glovebox, to a solution of 14 (5.2 mg, 0.0056 mmol) in 0.3 mL of DCM-$d_2$ in a silylated NMR tube was added a solution of $B(C_6F_5)_3$ (5.6 mg, 0.011 mmol) in 0.3 mL of DCM-$d_2$. An immediate color change to pale yellow occurred, and the mixture was capped with an NMR tube septum and sealed with electrical tape. The mixture was heated at 40° C. in an oil bath for 15 hours, at which point HNMR and FNMR spectra were recorded, indicating complete conversion to the desired product relative to [Au].

A solution of saturated aqueous sodium bicarbonate was injected through the septum, and the mixture was vigorously shaken. The septum was removed and the solution was diluted with water and dichloromethane. The organic layer was separated and the aqueous layer was washed 2× with DCM. The combined organic layers were dried over $MgSO_4$, filtered, and concentrated. The crude residue was purified by prep TLC (70:15:15 Hexanes/DCM/$Et_2O$) to afford the title compound (1.5 mg, 98% yield).

Reductive Elimination of BAY 59-3074 (Stoichiometric Borane)

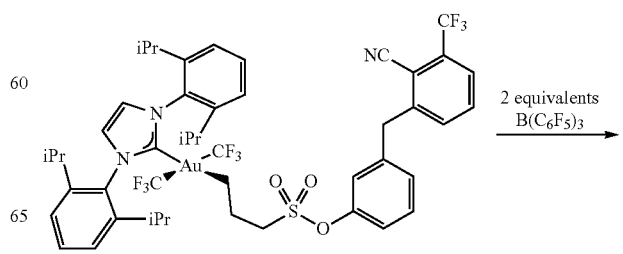

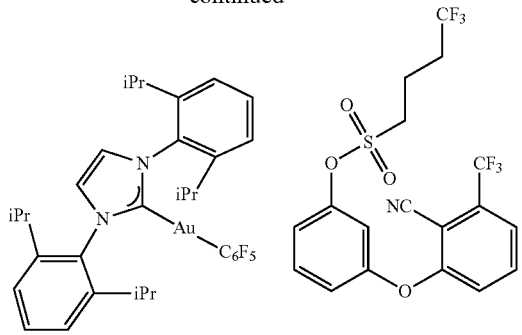

In a nitrogen filled glovebox, to a solution of 17 (22 mg, 0.02 mmol) in 0.5 mL of DCM-d$_2$ in a silylated NMR tube was added a solution of B(C$_6$F$_5$)$_3$ (20 mg, 0.04 mmol) in 0.5 mL of DCM-d$_2$. An immediate color change to pale yellow occurred, and the mixture was capped with an NMR tube septum and sealed with electrical tape. After 2 hours, HNMR and $^{19}$FNMR spectra were recorded, indicating complete conversion to the desired product relative to [Au].

A solution of saturated aqueous sodium bicarbonate was injected through the septum, and the mixture was vigorously shaken. The septum was removed and the solution was diluted with water and dichloromethane. The organic layer was separated and the aqueous layer was washed 2× with DCM. The combined organic layers were dried over MgSO$_4$, filtered, and concentrated. The crude residue was purified by prep TLC (6:2:2 Hexanes/DCM/Et$_2$O) to afford the title compound (6 mg, 67% yield).

Low Temperature NMR Reaction Monitoring

General Procedure for Kinetics

In a nitrogen filled glovebox, a solution of 1 (7.40 mg, 0.01 mmol in 400 μL DCM-d$_2$, prepared as a stock solution) was combined with 1-trifluoromethyl napthalene (internal standard, 1.96 mg, 0.01 mmol in 100 μL DCM-d$_2$, prepared as a stock solution) in a silylated NMR tube and fitted with a septum cap and sealed with electrical tape. In a separate septum-capped 2 dram vial was prepared a solution of B(C$_6$F$_5$)$_3$ in DCM-d$_2$ (102 mg in 1000 μL).

The two solutions were brought out of the glovebox and connected to N$_2$ atmosphere on a Schlenk line. The NMR tube solution was cooled to −78° C., and a portion of the B(C$_6$F$_5$)$_3$ solution (100 μL, 0.02 mmol) was added dropwise via syringe.

The mixture was agitated briefly, and then injected into a pre-cooled, tuned, and shimmed NMR probe at −15° C. FNMR scans were collected at 60 second intervals, utilizing one scan per time point.

Kinetic Traces

Figure 27:
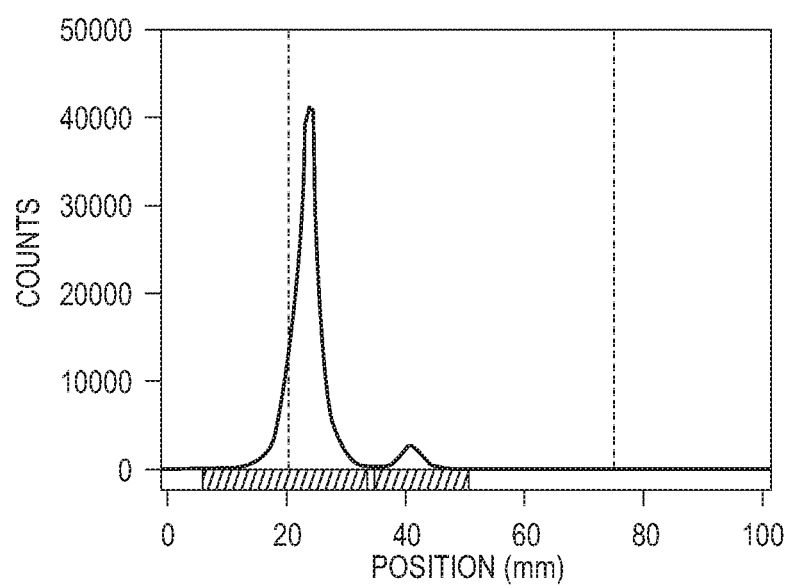
FIG. 27 illustrates a graphical representation of total counts of a first run for radiochemical conversion of [$^{18}$F]-3-(2-cyano-3-(trifluoromethyl)phenoxy)phenyl-4,4,4-trifluorobutane-1-sulfonate.
Figure 28:
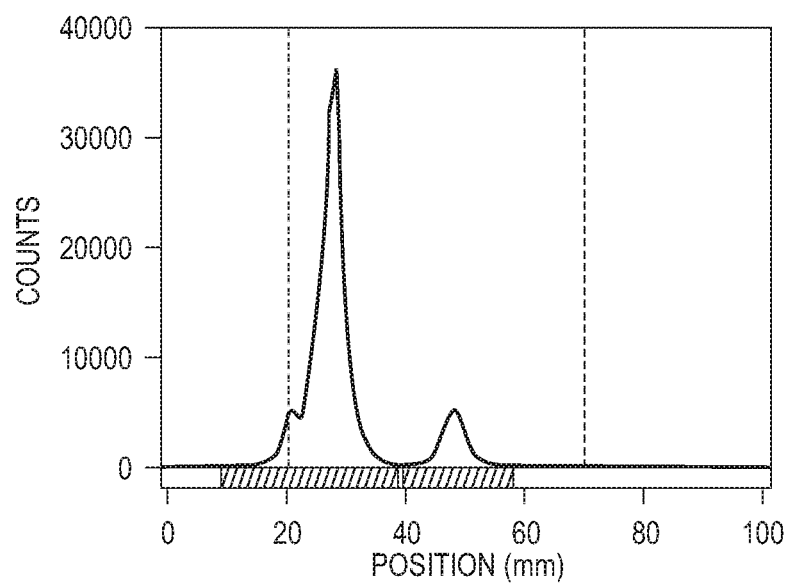
FIG. 28 illustrates a graphical representation of total counts of a second run for radiochemical conversion of [$^{18}$F]-3-(2-cyano-3-(trifluoromethyl)phenoxy)phenyl-4,4,4-trifluorobutane-1-sulfonate.

The data presented in FIGS. 24-27 represent three trials conducted using distinct drying methods for the DCM solvent, and the varying concentrations of observed intermediate (displaying 3:2 integrating, triplet/multiplet signals akin to 4) are taken as evidence for the formation of an intermediate aquo species. The data is represented as concentration (e.g., in mmol) of the species over time (e.g., in seconds). A small amount of a second isomer of this putative aquo is observed, in a direct parallel to 4, but its contribution to the overall mass balance is small at early reaction times. FIG. 28 illustrates an example of the concentration of species over time including isomer formation.

Under these conditions, IPrAuC$_6$F$_5$ does not form in substantial quantities until the mixture is warmed to room temperature. IPrAuCF$_3$ is not observed, potentially due to exchange broadening via reversible C—F abstraction.

Radiochemistry Cold Run

To a solution of 0.05M aqueous hydrofluoric acid (0.1 mL, 0.005 mmol) was added potassium carbonate (1.4 mg, 2 equiv) and Kryptofix [2.2.2] (3.8 mg, 2 equiv), and acetonitrile (0.4 mL). The mixture was concentrated at 30° C., and the process was repeated 2× with 0.4 mL of additional acetonitrile.

The resulting residue was extracted 2× with 0.1 mL of dichloromethane, and placed into a septum capped vial. After purging the headspace with nitrogen, a solution of 2 (12.7 mg, 5 equiv) in 0.3 mL of dichloromethane was added, followed by the corresponding [Au]—OAc complex (0.006 mmol) in 0.3 mL of DCM. The entire mixture was then transferred into a septum capped NMR tube.

Note that the spectra are not locked to deuterated solvent. Due to the longer reaction time for 23, IPrAuC$_6$F$_5$ is formed from IPrAuCF$_3$. Additionally, difluoroalkene resulting from elimination is seen in the reaction from 23.

Radiochemistry

No-carrier-added $^{18}$F-fluoride was produced by ~10 MeV proton irradiation of 97+% enriched [$^{18}$O]H$_2$O at low pressure in a Niobium target by the $^{18}$O (p,n)$^{18}$F nuclear reaction on the Biomedical Isotope Facility CTI RDS 111-DV001 cyclotron. The [$^{18}$O]H$_2$O/$^{18}$F$^-$ (25 μl) was transferred into a conical glass vial containing Kryptofix® 222 (3.5 mg, 9.3 μmol), and K$_2$CO$_3$ (0.375 mg, 2.7 μmol) in 400 μL of CH$_3$CN/H$_2$O. The water was removed by azeotropic distillation with anhydrous CH$_3$CN (0.4 mL) at 100° C. in vacuo, under a stream of nitrogen. The azeotropic drying process was repeated two additional times. Residual acetonitrile was found to substantially slow the reaction, so care was taken to thoroughly dry the remaining fluoride.

Figure 19:
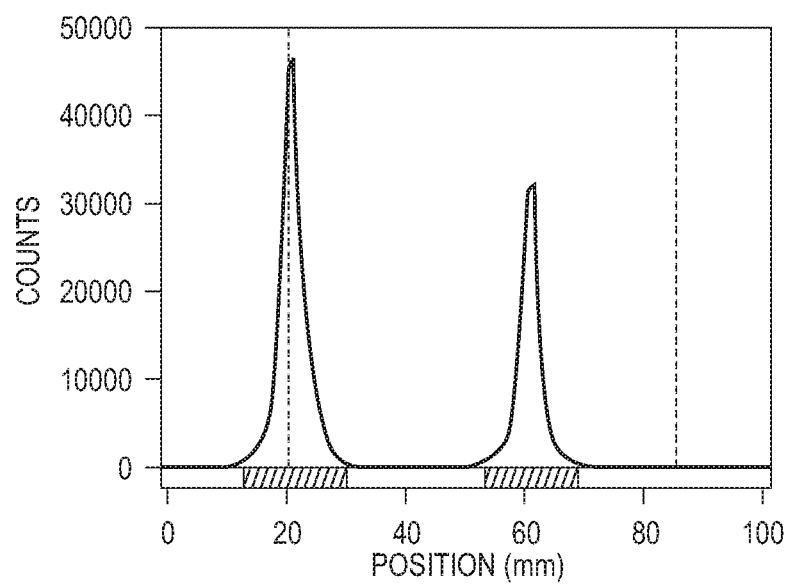
FIG. 19 illustrates a graphical representation of total counts of a first run for radiochemical conversion of [$^{18}$F]-1-(4-(4,4,4-trifluorobutyl)phenyl)ethan-1-one.
Figure 20:
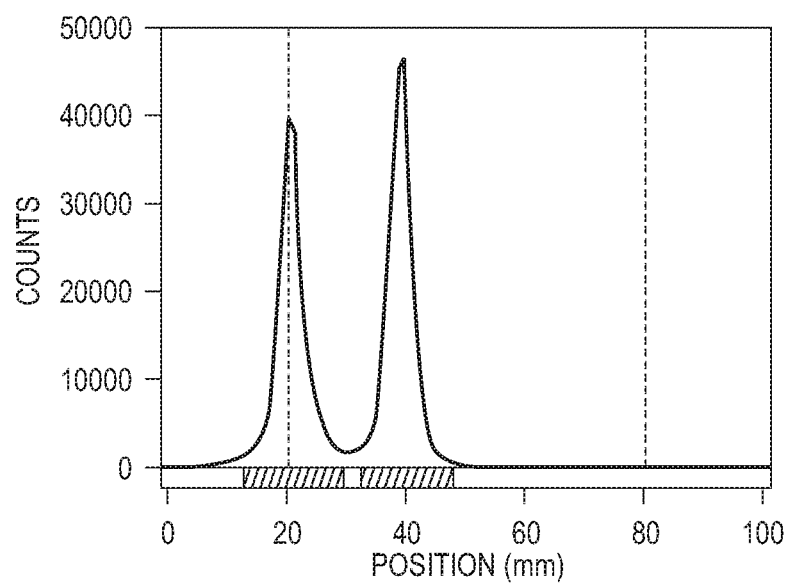
FIG. 20 illustrates a graphical representation of total counts of a second run for radiochemical conversion of [$^{18}$F]-1-(4-(4,4,4-trifluorobutyl)phenyl)ethan-1-one.
Figure 21:
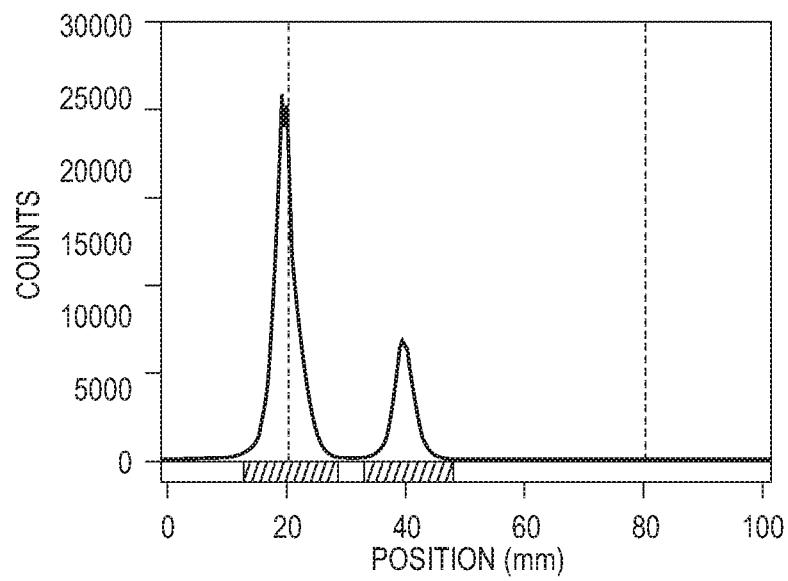
FIG. 21 illustrates a graphical representation of total counts of a third run for radiochemical conversion of [$^{18}$F]-1-(4-(4,4,4-trifluorobutyl)phenyl)ethan-1-one.
Figure 22:
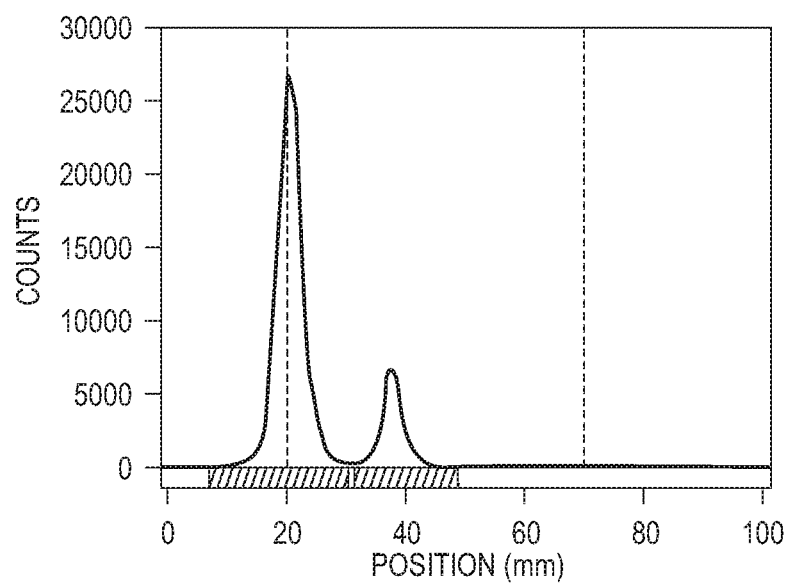
FIG. 22 illustrates a graphical representation of total counts of a fourth run for radiochemical conversion of [$^{18}$F]-1-(4-(4,4,4-trifluorobutyl)phenyl)ethan-1-one.
Figure 23:
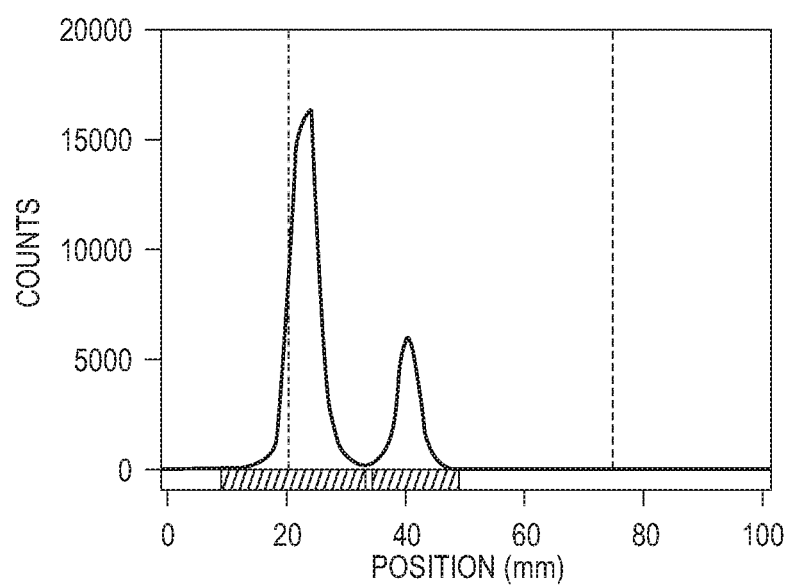
FIG. 23 illustrates a graphical representation of total counts of a fifth run for radiochemical conversion of [$^{18}$F]-1-(4-(4,4,4-trifluorobutyl)phenyl)ethan-1-one.
Figure 29:
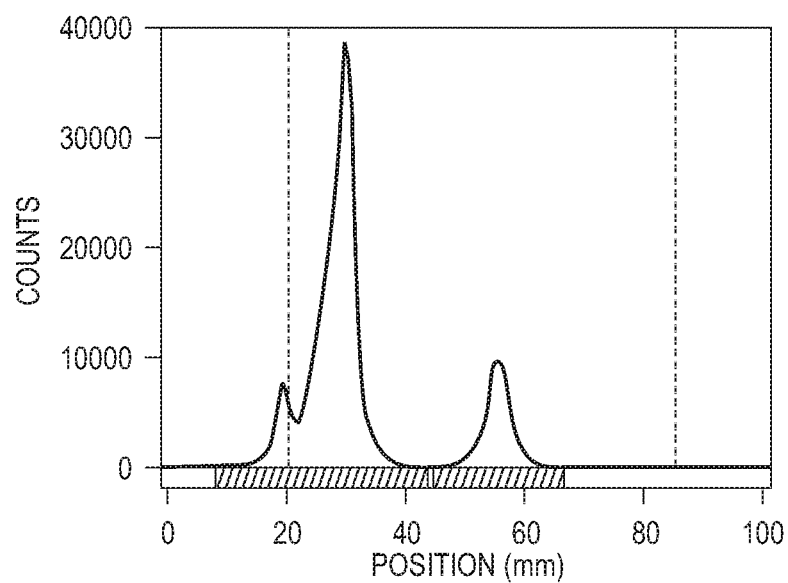
FIG. 29 illustrates a graphical representation of total counts of a third run for radiochemical conversion of [$^{18}$F]-3-(2-cyano-3-(trifluoromethyl)phenoxy)phenyl-4,4,4-trifluorobutane-1-sulfonate.

The residue was extracted with dichloromethane (2×0.1 mL) to a glass vial and capped with a septum cap. This transferred on average 88±1% of the radioactivity (n=11). Initial activities listed below are for the reaction vial post transfer, and total times include azeotropic drying. The headspace was purged with N$_2$ for 2 minutes, and a solution of tris(pentafluorophenyl)borane in dichloromethane (0.25 mL of 0.1 M solution, 25 μmol) was injected through the septum followed by a solution of the relevant Au(III) acetate complex (5 μmol) in dichrolomethane (0.25 mL). After the indicated reaction time, the solution was spotted onto a TLC plate, eluted with the indicated solvent mixture, and the radiochemical conversion was measured using a radio-TLC scanner (AR-2000 Imaging Scanner, Bioscan) as counts with identical retention as an authentic sample of the product as a fraction of total counts. The total counts for run 1 of the radiochemical conversion of [$^{18}$F]-1-(4-(4,4,4-trifluorobutyl)phenyl)ethan-1-one are illustrated in FIG. 19 with the corresponding table of data. The total counts for run 2 of the radiochemical conversion of [$^{18}$F]-1-(4-(4,4,4-trifluorobutyl)phenyl)ethan-1-one are illustrated in FIG. 20 with the corresponding table of data. The total counts for run 3 of the radiochemical conversion of [$^{18}$F]-1-(4-(4,4,4-trifluorobutyl)phenyl)ethan-1-one are illustrated in FIG. 21 with the corresponding table of data. The total counts for run 4 of the radiochemical conversion of [$^{18}$F]-1-(4-(4,4,4-trifluorobutyl)phenyl)ethan-1-one are illustrated in FIG. 22 with the corresponding table of data. The total counts for run 5 of the radiochemical conversion of [$^{18}$F]-1-(4-(4,4,4-trifluorobutyl)phenyl)ethan-1-one are illustrated in FIG. 23 with the corresponding table of data. The total counts for run 1 of the radiochemical conversion of [$^{18}$F]-5,5,5-trifluoropentyl 2-naphthoate are illustrated in FIG. 24 with the corresponding table of data. The total counts for run 2 of the radiochemical conversion of [$^{18}$F]-5,5,5-trifluoropentyl 2-naphthoate are illustrated in FIG. 25 with the corresponding table of data. The total counts for run 3 of the radiochemical conversion of [$^{18}$F]-5,5,5-trifluoropentyl 2-naphthoate are illustrated in FIG. 26 with the corresponding table of data. The total counts for run 1 (* Eluted twice with 30:70 Et$_2$O/Hex instead of once with 10:90) of the radio chemical conversion of [$^{18}$F]-3-(2-cyano-3-(trifluoromethyl)phenoxy)phenyl-4,4,4-trifluorobutane-1-sulfonate are illustrated in FIG. 27 with the corresponding table of data. The total counts for run 2 of the radio chemical conversion of [$^{18}$F]-3-(2-cyano-3-(trifluoromethyl)phenoxy)phenyl-4,4,4-trifluorobutane-1-sulfonate are illustrated in FIG. 28 with the corresponding table of data. The total counts for run 3 of the radio chemical conversion of [$^{18}$F]-3-(2-cyano-3-(trifluoromethyl)phenoxy)phenyl-4,4,4-trifluorobutane-1-sulfonate are illustrated in FIG. 29 with the corresponding table of data.

[$^{18}$F]-1-(4-(4,4,4-trifluorobutyl)phenyl)ethan-1-one

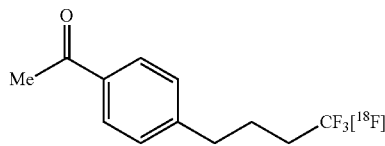

Reaction Time: 8 minutes
TLC solvent: 7:3 Hexanes/Diethyl Ether
The radiochemical conversions obtained were as follows for 5 trials:

TABLE 1

| Run | Initial Activity | Total Time | Radiochemical Conversion (TLC) | |
|---|---|---|---|---|
| 1 | 6.55 mCi | 24 min | 38.4% | |
| 2 | 1.30 mCi | 23 min | 52.0% | |
| 3 | 0.73 mCi | 22 min | 24.3% | 31.2 ± 13.8% |
| 4 | 0.72 mCi | 28 min | 18.4% | |
| 5 | 0.57 mCi | 32 min | 22.7% | |

[$^{18}$F]-5,5,5-trifluoropentyl 2-naphthoate

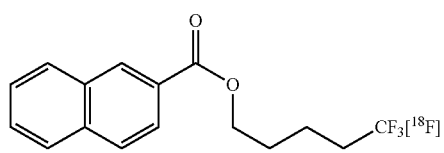

Reaction Time: 10 minutes
TLC solvent: 7:3 Hexanes/Diethyl Ether
The radiochemical conversions obtained were as follows for 3 trials:

TABLE 2

| Run | Initial Activity | Total Time | Radiochemical Conversion (TLC) | |
|---|---|---|---|---|
| 1 | 3.92 mCi | 40 min | 23.8% | |
| 2 | 1.79 mCi | 36 min | 23.3% | 26.8 ± 5.6% |
| 3 | 0.95 mCi | 44 min | 33.3% | |

[$^{18}$F]-3-(2-cyano-3-(trifluoromethyl)phenoxy)phenyl-4,4,4-trifluorobutane-1-sulfonate

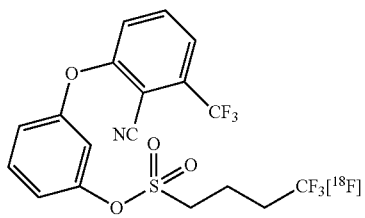

Reaction Time: 25 minutes
TLC solvent: 1:9 Hexanes/Diethyl Ether (Note: F—B (C$_6$F$_5$)$_3$ is mobile at this solvent polarity)
The radiochemical conversions obtained were as follows for 3 trials:

TABLE 3

| Run | Initial Activity | Total Time | Radiochemical Conversion (TLC) | |
|---|---|---|---|---|
| 1 | 5.06 mCi | 52 min | 6.3% | |
| 2 | 1.60 mCi | 56 min | 12.0% | 11.7 ± 5.3% |
| 3 | 1.11 mCi | 63 min | 16.9% | |

Isolation and Specific Activity of [$^{18}$F] BAY 59-3074

No-carrier-added $^{18}$F-fluoride was produced by ~10 MeV proton irradiation of 97+% enriched [$^{18}$O]H$_2$O at low pressure in a Niobium target by the $^{18}$O (p,n)$^{18}$F nuclear reaction on the Biomedical Isotope Facility CTI RDS 111-DV001 cyclotron. The [$^{18}$O]H$_2$O/$^{18}$F$^-$ (125 μl, 71.3 mCi) was transferred into a conical glass vial containing Kryptofix® 222 (3.5 mg, 9.3 μmol), and K$_2$CO$_3$ (0.375 mg, 2.7 μmol) in 400 μL of CH$_3$CN/H$_2$O. The water was removed by azeotropic distillation with anhydrous CH$_3$CN (0.4 mL) at 100° C. in vacuo, under a stream of nitrogen. The azeotropic drying process was repeated four additional times. Residual acetonitrile was found to substantially slow the reaction, so care was taken to thoroughly dry the remaining fluoride.

Figure 30:
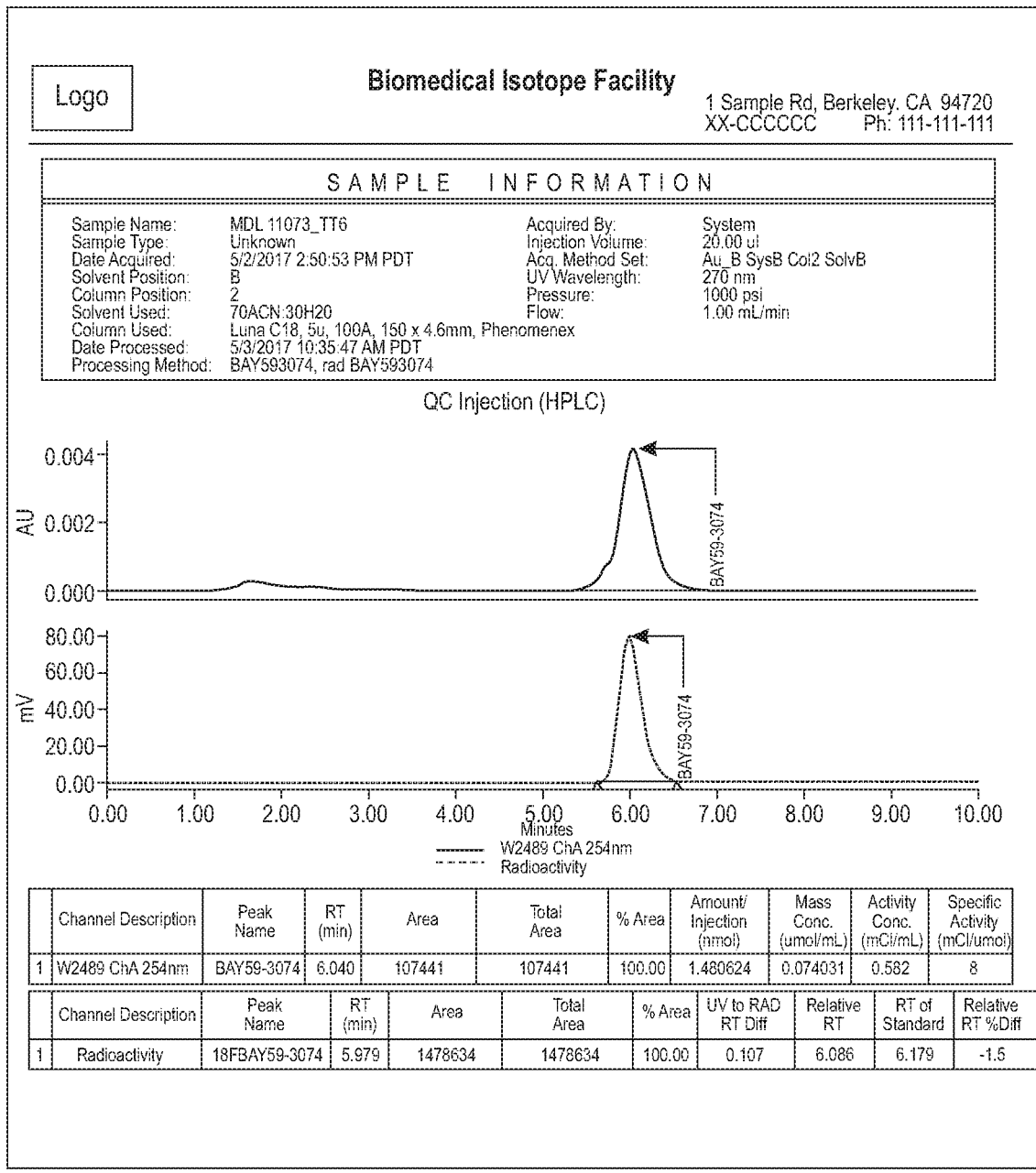
FIG. 30 illustrates a report of HPLC Analysis of isolated [$^{18}$F] BAY 59-3074.

The residue was extracted with dichloromethane (2×0.1 mL) to a glass vial and capped with a septum cap. (This transferred 86% of the radioactivity.) The headspace was purged with N$_2$ for 2 minutes, and a solution of tris(pentafluorophenyl)borane in dichloromethane (0.25 mL of 0.1 M solution, 25 μmol) was injected through the septum followed by a solution of 23 (5.8 mg, 5 μmol) in dichloromethane (0.25 mL). After 25 minutes, the reaction was concentrated to dryness, without heating, in vacuo. 1 mL of acetonitrile was added, and the mixture was diluted with 1 mL of H$_2$O and filtered through an alumina Sep-Pak (Water, Alumina N Plus Light Cartridge, 280 mg, 50-300 μm mesh). The vial was rinsed with an additional 1 mL of 1:1 MeCN/H$_2$O which was also filtered through the same alumina setpak. The filtrate was injected onto a prep HPLC column (Phenomenex Luna 10 μm, 100A C-18(2), 10×250 mm) and eluted at 5 mL/min with 70:30 MeCN/H$_2$O. The product was collected between 8.6 and 10 minutes, affording a 7 mL fraction totaling 3.94 mCi (decay corrected to the end of reaction, 6% RCY). This was analyzed by HPLC (Phenomenex Luna C18(2), 10 μm, 100A, 150×4.6 mm column, eluting 1 mL/min with 70:30 MeCN/H$_2$O), affording a specific activity measurement of 8 mCi/μmol based on a calibration curve determined using authentic BAY 59-3074. The report is reproduced in FIG. 30.

Table 4 below represents X-Ray crystallography data and structure refinement for compound 1a described above. Table 5 below represents X-Ray crystallography data and structure refinement for compound 1b described above. Table 6 below represents X-Ray crystallography data and structure refinement for compound 4 described above. Table 7 below represents X-Ray crystallography data and structure refinement for compound 5 described above. Table 8 below represents X-Ray crystallography data and structure refinement for compound 6 described above. Table 9 below represents X-Ray crystallography data and structure refinement for compound 7 described above. Table 10 below represents X-Ray crystallography data and structure refinement for compound 18 described above. Table 11 below represents X-Ray crystallography data and structure refinement for compound S2 described above. Table 12 below represents X-Ray crystallography data and structure refinement for compound S8 described above.

X-Ray Crystallography Data

TABLE 4

Crystal data and structure refinement for 1a.

| | |
|---|---|
| Identification code | shelx |
| Empirical formula | C30 H39 Au1 F6 N2 |
| Formula weight | 738.60 |
| Temperature | 100(2) K |
| Wavelength | 0.71073 Å |
| Crystal system | Orthorhombic |
| Space group | P b c a |
| Unit cell dimensions | a = 19.3702(6) Å alpha = 90°. |
| | b = 16.5858(5) Å beta = 90°. |
| | c = 37.4869(12) Å gamma = 90°. |
| Volume | 12043.4(6) Å$^3$ |
| Z | 17 |
| Density (calculated) | 1.629 Mg/m$^3$ |
| Absorption coefficient | 4.944 mm$^{-1}$ |
| F(000) | 5856 |
| Crystal size | 0.200 × 0.200 × 0.040 mm$^3$ |
| Theta range for data collection | 1.512 to 25.365°. |
| Index ranges | −21 <= h <= 23, −19 <= k <= 18, −45 <= l <= 45 |
| Reflections collected | 111842 |
| Independent reflections | 11032 [R(int) = 0.0468] |
| Completeness to theta = 25.000° | 100.0% |
| Absorption correction | Semi-empirical from equivalents |
| Max. and min. transmission | 0.646 and 0.457 |
| Refinement method | Full-matrix least-squares on F$^2$ |
| Data/restraints/parameters | 11032/0/721 |
| Goodness-of-fit on F$^2$ | 1.112 |
| Final R indices [I > 2sigma(I)] | R1 = 0.0325, wR2 = 0.0746 |
| R indices (all data) | R1 = 0.0401, wR2 = 0.0779 |
| Extinction coefficient | n/a |
| Largest diff. peak and hole | 3.291 and −0.739 e.Å$^{-3}$ |

TABLE 5

Crystal data and structure refinement for 1b.

| | |
|---|---|
| Identification code | shelx |
| Empirical formula | C21 H36 Au F6 P |
| Formula weight | 630.43 |
| Temperature | 100(2) K |
| Wavelength | 0.71073 Å |
| Crystal system | Orthorhombic |
| Space group | P n m a |
| Unit cell dimensions | a = 14.6624(5) Å a = 90°. |
| | b = 16.5973(5) Å b = 90°. |
| | c = 9.1732(3) Å g = 90°. |
| Volume | 2232.36(13) Å$^3$ |
| Z | 4 |
| Density (calculated) | 1.876 Mg/m$^3$ |
| Absorption coefficient | 6.716 mm$^{-1}$ |
| F(000) | 1240 |
| Crystal size | 0.300 × 0.240 × 0.200 mm$^3$ |
| Theta range for data collection | 2.454 to 25.347°. |
| Index ranges | −17 <= h <= 17, −19 <= k <= 19, −11 <= l <= 11 |
| Reflections collected | 40240 |
| Independent reflections | 2118 [R(int) = 0.0392] |
| Completeness to theta = 25.000° | 100.0% |
| Absorption correction | Semi-empirical from equivalents |
| Max. and min. transmission | 0.646 and 0.557 |
| Refinement method | Full-matrix least-squares on F$^2$ |
| Data/restraints/parameters | 2118/0/139 |
| Goodness-of-fit on F$^2$ | 1.143 |
| Final R indices [I > 2sigma(I)] | R1 = 0.0248, wR2 = 0.0586 |
| R indices (all data) | R1 = 0.0280, wR2 = 0.0602 |
| Extinction coefficient | n/a |
| Largest diff. peak and hole | 2.447 and −0.662 e.Å$^{-3}$ |

TABLE 6

Crystal data and structure refinement for 4.

| | |
|---|---|
| Identification code | shelx |
| Empirical formula | C30 H39 Au Br F5 N2 |
| Formula weight | 799.51 |
| Temperature | 100(2) K |
| Wavelength | 0.71073 Å |
| Crystal system | Monoclinic |
| Space group | P 21/n |
| Unit cell dimensions | a = 20.6333(15) Å, alpha = 90 deg. |
| | b = 9.9414(7) Å, beta = 107.3480(10) deg. |
| | c = 16.0121(12) Å, gamma = 90 deg. |
| Volume | 3135.1(4) Å$^3$ |
| Z | 4 |
| Density (calculated) | 1.694 Mg/m^3 |
| Absorption coefficient | 6.018 mm^−1 |
| F(000) | 1568 |
| Crystal size | 0.300 × 0.300 × 0.200 mm |
| Theta range for data collection | 2.068 to 25.359° |
| Index ranges | −24 <= h <= 24, −11 <= k <= 11, −19 <= l <= 1 |
| Reflections collected | 97533 |
| Independent reflections | 5736 [R(int) = 0.0269] |
| Completeness to theta = 25.000° | 100.0% |
| Absorption correction | Semi-empirical from equivalents |
| Max. and min. transmission | 0.745 and 0.588 |
| Refinement method | Full-matrix least-squares on F^2 |
| Data/restraints/parameters | 5736/0/348 |
| Goodness-of-fit on F$^2$ | 1.058 |
| Final R indices [I > 2sigma(I)] | R1 = 0.0300, wR2 = 0.0785 |
| R indices (all data) | R1 = 0.0313, wR2 = 0.0795 |
| Extinction coefficient | n/a |
| Largest diff. peak and hole | 2.261 and −1.658 e.Å$^{-3}$ |

TABLE 7

Crystal data and structure refinement for 5.

| | |
|---|---|
| Identification code | shelx |
| Empirical formula | C29 H36 Au Cl F6 N2 |
| Formula weight | 759.01 |

TABLE 7-continued

Crystal data and structure refinement for 5.

| | |
|---|---|
| Temperature | 100(2) K |
| Wavelength | 0.71073 Å |
| Crystal system | Monoclinic |
| Space group | P 21/n |
| Unit cell dimensions | a = 11.6081(6) Å, alpha = 90°. |
| | b = 17.2245(9) Å, beta = 105.5830(10)°. |
| | c = 15.6653(8) Å, gamma = 90°. |
| Volume | 3012.6(3) Å$^3$ |
| Z | 4 |
| Density (calculated) | 1.673 Mg/m$^3$ |
| Absorption coefficient | 5.030 mm$^{-1}$ |
| F(000) | 1496 |
| Crystal size | 0.100 × 0.080 × 0.040 mm$^3$ |
| Theta range for data collection | 1.796 to 25.409∞. |
| Index ranges | −13 <= h <= 14, −20 <= k <= 20, −18 <= l <= 18 |
| Reflections collected | 82795 |
| Independent reflections | 5531 [R(int) = 0.0823] |
| Completeness to theta = 25.000∞ | 100.0% |
| Absorption correction | Semi-empirical from equivalents |
| Refinement method | Full-matrix least-squares on F$^2$ |
| Data/restraints/parameters | 5531/0/369 |
| Goodness-of-fit on F$^2$ | 1.056 |
| Final R indices [I > 2sigma(I)] | R1 = 0.0428, wR2 = 0.0956 |
| R indices (all data) | R1 = 0.0564, wR2 = 0.1031 |
| Extinction coefficient | n/a |
| Largest diff. peak and hole | 3.188 and −1.027 e.≈$^{-3}$ |

TABLE 8

Crystal data and structure refinement for 6.

| | |
|---|---|
| Identification code | shelx |
| Empirical formula | C32 H41 Au F6 N2 |
| Formula weight | 764.63 |
| Temperature | 100(2) K |
| Wavelength | 0.71073 Å |
| Crystal system | Orthorhombic, P b c a |
| Unit cell dimensions | a = 16.3403(11) Å, alpha = 90 deg. |
| | b = 17.0007(11) Å, beta = 90 deg. |
| | c = 23.2921(15) Å, gamma = 90 deg. |
| Volume | 6470.5(7) A$^3$ |
| Z | 8 |
| Density (calculated) | 1.570 Mg/m$^3$ |
| Absorption coefficient | 4.605 mm$^-1$ |
| F(000) | 3040 |
| Crystal size | 0.200 × 0.100 × 0.100 mm |
| Theta range for data collection | 1.749 to 25.390° |
| Index ranges | −19 <= h <= 19, −20 <= k <= 20, −28 <= l <= 28 |
| Reflections collected | 144595 |
| Independent reflections | 5953 [R(int) = 0.0352] |
| Completeness to theta = 25.000° | 100.0% |
| Refinement method | Full-matrix least-squares on F$^2$ |
| Data/restraints/parameters | 5953/0/370 |
| Goodness-of-fit on F$^2$ | 1.155 |
| Final R indices [I > 2sigma(I)] | R1 = 0.0309, wR2 = 0.0753 |
| R indices (all data) | R1 = 0.0341, wR2 = 0.0774 |
| Extinction coefficient | n/a |
| Largest diff. peak and hole | 3.800 and −1.210 e.Å$^{-3}$ |

TABLE 9

Crystal data and structure refinement for 7.

| | |
|---|---|
| Identification code | shelx |
| Empirical formula | C40 H49 Au F6 N2 O |
| Formula weight | 884.78 |
| Temperature | 100(2) K |
| Wavelength | 0.71073 Å |
| Crystal system | Monoclinic, P 21/n |

TABLE 9-continued

Crystal data and structure refinement for 7.

| | |
|---|---|
| Unit cell dimensions | a = 12.1671(6) Å, alpha = 90 deg. |
| | b = 22.4672(11) Å, beta = 105.4170(10) deg. |
| | c = 14.5163(7) Å, gamma = 90 deg. |
| Volume | 3825.4(3) A$^3$ |
| Z | 4 |
| Density (calculated) | 1.536 Mg/m$^3$ |
| Absorption coefficient | 3.908 mm$^-1$ |
| F(000) | 1776 |
| Crystal size | 0.200 × 0.120 × 0.100 mm |
| Theta range for data collection | 1.714 to 25.373° |
| Index ranges | −14 <= h <= 14, −26 <= k <= 27, −17 <= l <= 17 |
| Reflections collected | 114481 |
| Independent reflections | 7027 [R(int) = 0.0374] |
| Completeness to theta = 25.000° | 100.0% |
| Refinement method | Full-matrix least-squares on F$^2$ |
| Data/restraints/parameters | 7027/0/451 |
| Goodness-of-fit on F$^2$ | 1.138 |
| Final R indices [I > 2sigma(I)] | R1 = 0.0341, wR2 = 0.0788 |
| R indices (all data) | R1 = 0.0386, wR2 = 0.0823 |
| Extinction coefficient | n/a |
| Largest diff. peak and hole | 3.633 and −1.245 e.Å$^{-3}$ |

TABLE 10

Crystal data and structure refinement for 18.

| | |
|---|---|
| Identification code | shelx |
| Empirical formula | C40 H49 Au Br F5 N2 O |
| Formula weight | 945.69 |
| Temperature | 100(2) K |
| Wavelength | 0.71073 Å |
| Crystal system | Monoclinic, P 21/c |
| Unit cell dimensions | a = 9.2424(3) Å, alpha = 90 deg. |
| | b = 20.6341 (6) Å, beta = 101.456(2) deg. |
| | c = 23.2072(6) Å, gamma = 90 deg. |
| | 4337.6(2) A$^3$ |
| Z | 4 |
| Density (calculated) | 1.448 Mg/m$^3$ |
| Absorption coefficient | 4.364 mm$^-1$ |
| F(000) | 1880 |
| Crystal size | 0.300 × 0.100 × 0.100 mm |
| Theta range for data collection | 1.332 to 25.386° |
| Index ranges | −11 <= h <= 11, −24 <= k <= 24, −27 <= l <= 27 |
| Reflections collected | 99742 |
| Independent reflections | 7958 [R(int) = 0.0791] |
| Completeness to theta = 25.000° | 100.0% |
| Absorption correction | None |
| Refinement method | Full-matrix least-squares on F$^2$ |
| Data/restraints/parameters | 7958/48/497 |
| Goodness-of-fit on F$^2$ | 1.148 |
| Final R indices [I > 2sigma(I)] | R1 = 0.0585, wR2 = 0.1599 |
| R indices (all data) | R1 = 0.0768, wR2 = 0.1675 |
| Extinction coefficient | n/a |
| Largest diff. peak and hole | 1.928 and −0.625 e.Å$^{-3}$ |

TABLE 11

Crystal data and structure refinement for S2.

| | |
|---|---|
| Identification code | shelx |
| Empirical formula | C27 H23 Au F6 I P |
| Formula weight | 816.29 |
| Temperature | 100(2) K |
| Wavelength | 0.71073 Å |
| Crystal system | Monoclinic |
| Space group | P 21/n |

TABLE 11-continued

Crystal data and structure refinement for S2.

| | |
|---|---|
| Unit cell dimensions | a = 7.5619(3) Å, a = 90°. |
| | b = 14.3616(5) Å, b = 95.4860(10)°. |
| | c = 24.1182(9) Å, g = 90° |
| Volume | 2607.26(17) Å$^3$ |
| Z | 4 |
| Density (calculated) | 2.080 Mg/m$^3$ |
| Absorption coefficient | 6.946 mm$^{-1}$ |
| F(000) | 1544 |
| Crystal size | 0.500 × 0.500 × 0.500 mm$^3$ |
| Theta range for data collection | 1.652 to 25.361° |
| Index ranges | −9 <= h <= 9, −17 <= k <= 17, −29 <= l <= 29 |
| Reflections collected | 73049 |
| Independent reflections | 4778 [R(int) = 0.0341] |
| Completeness to theta = 25.000° | 100.0% |
| Absorption correction | Semi-empirical from equivalents |
| Max. and min. transmission | 0.745 and 0.588 |
| Refinement method | Full-matrix least-squares on F$^2$ |
| Data/restraints/parameters | 4778/0/325 |
| Goodness-of-fit on F$^2$ | 1.130 |
| Final R indices [I > 2sigma(I)] | R1 = 0.0204, wR2 = 0.0481 |
| R indices (all data) | R1 = 0.0211, wR2 = 0.0484 |
| Extinction coefficient | n/a |
| Largest diff. peak and hole | 1.471 and −0.799 e.Å$^{-3}$ |

TABLE 12

Crystal data and structure refinement for S8.

| | |
|---|---|
| Identification code | shelx |
| Empirical formula | C33 H43 Au F6 N2 |
| Formula weight | 778.66 |
| Temperature | 100(2) K |
| Wavelength | 0.71073 A |
| Crystal system, space group | Orthorhombic, P b c a |
| Unit cell dimensions | a = 15.9214(14) A alpha = 90 deg. |
| | b = 17.6740(15) A beta = 90 deg. |
| | c = 23.278(2) A gamma = 90 deg. |
| Volume | 6550.2(10) A$^3$ |
| Z, Calculated density | 8, 1.579 Mg/m$^3$ |
| Absorption coefficient | 4.550 mm$^{-1}$ |
| F(000) | 3104 |
| Crystal size | 0.140 × 0.060 × 0.060 mm |
| Theta range for data collection | 1.750 to 25.384 deg. |
| Limiting indices | −19 <= h <= 19, −21 <= k <= 21, −28 <= l <= 28 |
| Reflections collected/unique | 214909/6017 [R(int) = 0.0352] |
| Completeness to theta = 25.000 | 100.0% |
| Absorption correction | None |
| Refinement method | Full-matrix least-squares on F$^2$ |
| Data/restraints/parameters | 6017/6/379 |
| Goodness-of-fit on F$^2$ | 1.157 |
| Final R indices [I > 2sigma(I)] | R1 = 0.0345, wR2 = 0.0741 |
| R indices (all data) | R1 = 0.0393, wR2 = 0.0780 |
| Extinction coefficient | n/a |
| Largest diff. peak and hole | 3.893 and −1.409 e.A$^{-3}$ |

While various embodiments have been described above, it should be understood that they have been presented by way of example only, and not limitation. Thus, the breadth and scope of a preferred embodiment should not be limited by any of the above-described exemplary embodiments, but should be defined only in accordance with the following claims and their equivalents.

What is claimed is:

1. A precursor formed from a gold type 3 (Au(III)) complex, comprising:
   Au(CF$_3$)(CF$_2$R)LX via activation of Au(CF$_3$)$_2$LR with bromotrimethylsilane (Me$_3$SiBr), wherein C comprises carbon, F comprises fluoride, L comprises isopropyl (IPr) or tricyclohexylphosphine (P(Cy)$_3$), R comprises an organic substituent, and X comprises bromine (Br).

2. A method, comprising:
   activating a gold type 3 (Au(III)) complex comprising Au(CF$_3$)$_2$LR, wherein C comprises carbon, F comprises fluoride, L comprises isopropyl (IPr) or tricyclohexylphosphine (P(Cy)$_3$) and R comprises an organic substituent with bromotrimethylsilane (Me$_3$SiBr) to form a precursor comprising Au(CF$_3$)(CF$_2$R)LX, wherein X comprises bromine (Br); and
   performing a ligand exchange on the precursor.

3. The method of claim 2, further comprising:
   applying a radiochemistry procedure on the precursor to produce a trifluoromethyl containing positron emission tomography (PET) tracer.

4. The method of claim 3, wherein the PET tracer comprises RF$_3$[$^{18}$F].

5. The method of claim 2, wherein the activating is performed at 80 degrees Celsius.

6. The method of claim 2, wherein X comprises bromine and performing the ligand exchange comprises:
   replacing the bromine with acetate.

7. The method of claim 6, wherein the ligand exchange is performed with AgOAc, dichloromethane, and methylhydroxide.

* * * * *